(12) United States Patent
Wischik et al.

(10) Patent No.: US 11,344,558 B2
(45) Date of Patent: *May 31, 2022

(54) 3, 7-DIAMINO-10H-PHENOTHIAZINE SALTS AND THEIR USE

(71) Applicant: WisTa Laboratories Ltd., Singapore (SG)

(72) Inventors: Claude Michel Wischik, Aberdeen (GB); Janet Elizabeth Rickard, Aberdeen (GB); Charles Robert Harrington, Aberdeen (GB); David Horsley, Aberdeen (GB); John Mervyn David Storey, Old Aberdeen (GB); Colin Marshall, Old Aberdeen (GB); James Peter Sinclair, Old Aberdeen (GB); Thomas Craven Baddeley, Old Aberdeen (GB)

(73) Assignee: WisTa Laboratories Ltd., Singapore (SG)

(*) Notice: Subject to any disclaimer, the term of this patent is extended or adjusted under 35 U.S.C. 154(b) by 99 days.

This patent is subject to a terminal disclaimer.

(21) Appl. No.: 14/929,111

(22) Filed: Oct. 30, 2015

(65) Prior Publication Data
US 2016/0051559 A1 Feb. 25, 2016

Related U.S. Application Data

(60) Division of application No. 14/248,730, filed on Apr. 9, 2014, now Pat. No. 9,174,954, which is a continuation of application No. 13/011,797, filed on Jan. 21, 2011, now Pat. No. 8,710,051, which is a continuation of application No. 12/294,599, filed as application No. PCT/GB2007/001103 on Mar. 28, 2007, now Pat. No. 7,888,350.

(60) Provisional application No. 60/786,690, filed on Mar. 29, 2006.

(51) Int. Cl.
| | |
|---|---|
| *A61K 31/5415* | (2006.01) |
| *C07D 279/22* | (2006.01) |
| *C07D 279/20* | (2006.01) |
| *C09B 21/00* | (2006.01) |

(52) U.S. Cl.
CPC ........ *A61K 31/5415* (2013.01); *C07D 279/20* (2013.01); *C07D 279/22* (2013.01); *C09B 21/00* (2013.01); *Y02A 50/30* (2018.01)

(58) Field of Classification Search
CPC .............. A61K 31/5415; C07D 279/22; C07D 279/20; C09B 21/00
See application file for complete search history.

(56) References Cited

U.S. PATENT DOCUMENTS

| | | | |
|---|---|---|---|
| 2,928,767 A | 3/1960 | Gulesich et al. | |
| 4,309,255 A | 1/1982 | Gendler et al. | |
| 4,622,395 A | 11/1986 | Bellus et al. | |
| 4,647,525 A | 3/1987 | Miller | |
| 5,095,011 A | 3/1992 | Kaplan et al. | |

(Continued)

FOREIGN PATENT DOCUMENTS

| | | |
|---|---|---|
| DE | 44 03 091 | 8/1994 |
| DE | 44 30 091 A1 | 2/1996 |

(Continued)

OTHER PUBLICATIONS

Mayo Clinic 2010.*
Giorgini et al. Genome Biology 2005, 6:210.*
Jellinger The ScientificWorld J. (2011) 11, 1893-1907.*
Ross et al. Momecular cell Biol 6, 2005, 891-898.*
Butterfield et al. Mechanisms of Ageing and Development 122 (2001) 945-962.*
U.S. Appl. No. 60/945,006, filed Jun. 19, 2007.
U.S. Appl. No. 60/960,544, filed Oct. 3, 2007.
U.S. Appl. No. 60/996,177, filed Nov. 5, 2007.
U.S. Appl. No. 61/077,281, filed Jul. 1, 2008.
Aizawa et al., "Microtubule-binding domain of tau proteins," Journal of Biological Chemistry, 1988, vol. 263, pp. 7703-7707.

(Continued)

*Primary Examiner* — Shirley V Gembeh
(74) *Attorney, Agent, or Firm* — Wolf, Greenfield & Sacks, P.C.

(57) ABSTRACT

Described are methods of preparing reduced 3,7-diamino-10H-phenothiazine (DAPTZ) compounds of formula:

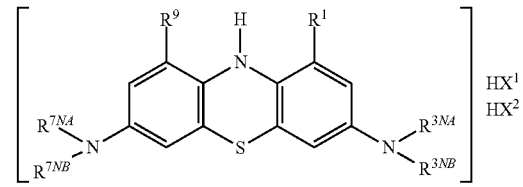

wherein: $R^1$ and $R^9$ are independently selected from: —H; $C_{1-4}$alkyl; $C_{2-4}$alkenyl; and halogenated $C_{1-4}$alkyl; each of $R^{3NA}$ and $R^{3NB}$ is independently selected from: —H; $C_{1-4}$alkyl; $C_{2-4}$alkenyl; and halogenated $C_{1-4}$alkyl; each of $R^{7NA}$ and $R^{7NB}$ is independently selected from: —H; $C_{1-4}$alkyl; $C_{2-4}$alkenyl; and halogenated $C_{1-4}$alkyl; each of $HX^1$ and $HX^2$ is independently a protic acid; and pharmaceutically acceptable salts, solvates, and hydrates thereof. These methods are particularly useful for producing stable reduced forms, and with high purity. The stability and purity are especially relevant for pharmaceutical compositions for the treatment of disease. The compounds are useful for treatment of e.g. tauopathies, such as Alzheimer's disease, and also as prodrugs for the corresponding oxidized thioninium drugs.

11 Claims, 5 Drawing Sheets

(56) References Cited

U.S. PATENT DOCUMENTS

| | | | |
|---|---|---|---|
| 5,220,009 | A | 6/1993 | Mazur et al. |
| 5,693,638 | A | 12/1997 | Myers |
| 5,827,644 | A | 10/1998 | Floyd et al. |
| 6,953,794 | B2 | 10/2005 | Wischik et al. |
| 6,953,974 | B2 | 10/2005 | Rathfelder et al. |
| 7,888,350 | B2 | 2/2011 | Wischik et al. |
| 8,263,589 | B2 | 9/2012 | Wischik et al. |
| 8,710,051 | B2 | 4/2014 | Wischik et al. |
| 9,149,481 | B2 | 10/2015 | Wischik et al. |
| 2002/0103189 | A1 | 8/2002 | Miyamoto et al. |
| 2002/0168687 | A1 | 11/2002 | Wischik et al. |
| 2002/0197258 | A1 | 12/2002 | Ghanbari et al. |
| 2003/0181389 | A1 | 9/2003 | Wülfert et al. |
| 2005/0136110 | A1 | 6/2005 | Bartholomaeus et al. |
| 2006/0014216 | A1 | 1/2006 | Wischik et al. |
| 2006/0287523 | A1 | 12/2006 | Wischik et al. |
| 2007/0116757 | A1 | 5/2007 | Rariy et al. |

FOREIGN PATENT DOCUMENTS

| | | |
|---|---|---|
| EP | 0 457 295 A3 | 11/1991 |
| EP | 0 618 968 B1 | 10/1994 |
| EP | 0 737 671 A2 | 10/1996 |
| EP | 0 909 814 A2 | 4/1999 |
| EP | 0 911 390 A2 | 4/1999 |
| EP | 0 911 398 A2 | 4/1999 |
| EP | 1 067 386 | 10/2001 |
| FR | 2788436 | 7/2000 |
| JP | 06-289015 | 10/1994 |
| WO | WO-89/03993 | 5/1989 |
| WO | WO 89/03993 A1 | 5/1989 |
| WO | WO-93/03177 | 2/1993 |
| WO | WO-93/03369 | 2/1993 |
| WO | WO-93/11231 | 6/1993 |
| WO | WO-95/05466 | 2/1995 |
| WO | WO-95/05601 | 2/1995 |
| WO | WO-96/04915 | 2/1996 |
| WO | WO-96/05837 | 2/1996 |
| WO | WO-96/30766 A | 10/1996 |
| WO | WO-98/31219 | 7/1998 |
| WO | WO-99/62548 | 12/1999 |
| WO | WO 99/62548 A1 | 12/1999 |
| WO | WO-01/53340 | 7/2001 |
| WO | WO-02/03972 | 1/2002 |
| WO | WO-02/04025 | 1/2002 |
| WO | WO-02/055720 A2 | 7/2002 |
| WO | WO-02/059150 A2 | 8/2002 |
| WO | WO-02/075318 A2 | 9/2002 |
| WO | WO-03/007933 A1 | 1/2003 |
| WO | WO-2005/030676 A1 | 4/2005 |
| WO | WO 2005/054217 A1 | 6/2005 |
| WO | WO-2006/032879 A2 | 3/2006 |
| WO | WO 2006/032879 A2 | 3/2006 |
| WO | WO-2007/110629 A1 | 10/2007 |

OTHER PUBLICATIONS

Allen et al., "Further clinical experience with toluidine blue and protamine sulfate", Abnormal Bleeding II, pp. 692-703.

Anderton et al., "Dendritic Changes in Alzheimer's Disease and Factors That May Underlie these Changes," Prog. Neurobiol., Aug. 1998., pp. 595-609, vol. 55, No. 6.

Avila et al., Assorted Proteins, Harwood Aend Publishers, Amsterdam, 1997.

Bancher et al., "Accumulation of abnormally phosphorylated T precedes the formation of neurofibrillary tangles in Alzheimer's disease," Brain Research, 1989, vol. 477, pp. 90-99.

Biernat et al., "The switch of tau protein to an Alzheimer-like state includes the phosphorylation of two serine-proline motifs upstream of the microtubule binding region," EMBO Journal 11, 1992, pp. 1593-1597.

Bondareff, et al. "Immunohistochemical staging of neurofibrillary degeneration in Alzheimer's disease", Journal of Neuropathology and Experimental Neurology (Mar. 1994), vol. 53, No. 2, pp. 158-164.

Braak et al., "Alzheimer's Disease: Transiently Developing Dendritic Changes in Pyramidal Cells of Sector CA1 of the Ammon's Horn," Acta Neuropathol., 1997, pp. 323-325, vol. 93.

Brandt R., "Cytoskeletal Mechanisms of Axon Outgrowth and Pathfinding," Cell Tissue Res., 1998, pp. 181-189, vol. 292.

Brion et al., "Characterization of a Partial cDNA Specific for the High Molecular Weight Microtubule-Associated Protein MAP2 That Encodes Epitopes Shared with Paired Helical Filaments of Alzheimer's Disease," Dementia, 1990, pp. 304-315, vol. 1.

Callaway et al, "Methylene blue restores spatial memory retention impaired by an inhibitor of cytochrome oxidase in rats", Neuroscience Letters, 332, (2002), pp. 83-86.

Caputo et al., "Amyloid-like properties of a synthetic peptide corresponding to the carboxy terminus of ((-amyloid protein precursor," Archives of Biochemistry and Biophysics, 1992, vol. 292, pp. 199-205.

Caputo et al., "The amyloid proteins of Alzheimer's disease as potential targets for drug therapy," Neurobiology of Aging, vol. 10, 1989, pp. 451-461.

Caputo et al., "The amyloid proteins of Alzheimer's disease as potential targets for drug therapy," Neurobiology of Aging, vol. 10, pp. 451-461.

Cecil Textbook of Medicine (20th Edition, vol. 2, 1996, pp. 1739-1747).

Condamines et al., "New immunoassay for the mapping of neurofibrillary degeneration in Alzheimer's disease using two monoclonal antibodies against human paired helical filament tau proteins," Neuroscience Letters, Jun. 9, 1995, vol. 192, No. 2, pp. 81-84.

Cudd et al., "Pharmacokinetics and toxicity of tolonium chloride in sheet", Vet Human Toxicol, 38(5), Oct. 1996, pp. 329-334.

Day R., "How to Write and Publish a Scientific Paper," 1983, pp. 124-127, ISI Press, Philadelphia, PA.

De Ancos et al., Journal of Biological Chemistry, 1993, pp. 7976-7982, vol. 268(11).

DeTure et al., "In vitro assembly of Alzheimer-like filaments. How a small cluster of charged residues in tau and MAP2 controls filament morphology," Journal of Biological Chemistry, 2002, vol. 277, p. 34755-34759.

Epstein, J.B. et al, "The utility of toluidine blue application as a diagnostic aid in patients previously treated for upper oropharyngeal carcinoma", Oral medicine, (1997), pp. 537-547, vol. 83, No. 5.

Fasulo et al., "Overexpression of Alzheimer's PHF core tau fragments: implications for the tau truncation hypothesis," Rapid Science Publishers, Alzheimer's Research, vol. 2, No. 5, pp. 195-200, Oct. 1996.

Friedhoff et al., Biochemistry, 1998, p. 10223-10230, vol. 37.

Friedhoff et al., PNAS, 1998, p. 15712-15717, vol. 95.

Garcini et al., "In Vitro Conditions for the Self-Polymerization of the Microtubule-Associated Protein, Tau Factor," J. Biochem., 1987, pp. 1415-1421, vol. 102, No. 6.

Garcini et al., Self Assembly of Microtubule Associated Protein TAU into Filaments Resembling those found in Alzheimer Disease, Biochemical and Biophysical Research Communications, 1988, pp. 790-797.

Garcini et al., "Tau Factor Polymers are Similar to Paired Helical Filaments of Alzheimer's Disease," 1988, pp. 150-154, Elsevier Science Publishers B.V.

Gavezzotti, "Are Crystal Structures Predictable?" Accounts of Chemical Research, vol. 27, pp. 309-314(1994).

Gertz, et al. "Examination of the validity of the hierarchical model of neuropathological staging in normal aging and Alzheimer's disease", Aeta Neuropathol (1998), vol. 95, pp. 154-158.

Gertz, et al. "The relationship between clinical dementia and neuropathological staging (Braak) in a very elderly community sample", Eur Arch Psychiatry Clin Neurosci (1996) vol. 246, pp. 132-136.

Giannetti et al., "Fibers of tau fragments, but not full length tau, exhibit a cross (-structure: implications for the formation of paired helical filaments," Protain Science, 2000, vol. 9, pp. 2427-2435.

(56) References Cited

OTHER PUBLICATIONS

Goedert et al., "Tau Proteins of Alzheimer Paired Helical Filaments: Abnormal Phosphorylation of All Six Brain Isoforms," Neuron, Jan. 1992, pp. 159-168, vol. 8.

Goedert M. et al., "Cloning and sequencing of the cDNA encoding a core protein of the paired helical filament of Alzheimer disease: Identification as the microtubule-associated protein tau," Proc. Natl. Acad. Sci. USA, Jun. 1988, vol. 85, pp. 4051-4055.

Gotz et al., "Tau filaments formation in transgenic mice expressing P301L tau," J. Biol. Chem., Jan. 5, 2001, vol. 276(1), pp. 529-534.

Grover et al., "5' Splice Site Mutations in Tau Associated with the Inherited Dementia FTDP-17 Affect a Stem-Loop Structure That Regulates Alternative Splicing of Exon 10*," The Journal of Biological Chemistry, May 21, 1999 Issue, p. 15134-15143, vol. 274, No. 21.

Grundke-Iqbal et al., "Abnormal phosphorylation of microtubule-associated protein T (tau) in Alzheimer cytoskeletal pathology," Proc. Natl. Acad. Sci. USA, 1986, vol. 83, pp. 4913-4917.

Hagestedt et al., "Tau protein becomes long and stiff upon phosphorylation: correlation between paracrystalline structure and degree of phosphorylation," The Journal of cell biology, 1989, vol. 109, pp. 1643-1651.

Harada et al., "Altered Microtubule Organization in Small-Calibre Axons of Mice Lacking Tau Protein," Letters to Nature (no date available).

Harada et al., "Altered Microtubule Organization in Small-Calibre Axons of Mice Lacking Tau Protein," Letters to Nature, vol. 369, 1994, pp. 488-489.

Harrington et al., "Competitive ELISA for the Measurement of Tau Protein in Alzheimer's Disease," Journal of Immunological Methods, 1990, pp. 261-271, vol. 134.

Harrington et al., "Measurement of Distinct Immunochemical Presentations of Tau Protein in Alzheimer Disease," Proc. Natl. Acad. Sci., Jul. 1991, pp. 5842-5846, vol. 88.

Holoubek et al., "Toluidine blue in bleeding associated with thrombopenia", J.A.M.A., Jan. 22, 1949, vol. 139, No. 4, pp. 214-216.

Hutton et al., "Association of Missense and 5'-splice-site Mutations in Tau With the Inherited Dementia FTDP-17," Nature, Jun. 18, 1998, pp. 702-705, vol. 393.

International Search Report for PCT/GB2007/001103 dated Aug. 30, 2007 (4 pgs.).

Ishiguro et al., "A novel tubulin-dependent protein kinase forming a paired helical filament epitope on tau," J. Biochem, 1988, vol. 104, pp. 319-321.

Ishiguro et al., "A serine/threonine proline kinase activity is included in the tau protein kinase fraction forming a paired helical filament epitope," Neuroscience Letters, 1991, vol. 128, pp. 195-198.

Ishiguro et al., "Phosphorylation sites on tau by tau protein kinase I, a bovine derived kinase generating an epitope of paired helical filaments," Neuroscience Letters, 1992, vol. 148, pp. 202-206.

Ishiguro et al., "Tau protein kinase I converts normal tau protein into A68-like component of paired helical filaments," Journal of Biological Chemistry, 1992, vol. 267, p. 10897-10901.

Ishihara et al., "Age-Dependent Emergence and Progression of a Tauopathy in Transgenic Mice Overexpressing the Shortest Human Tau Isoform," Neuron, Nov. 1999, pp. 751-762, vol. 24.

Ito, A. et al., "Enhancing effect of ascorbate on toluidine blue-photosensitization of yeast cells" Photochemistry and Photobiology, (1982), pp. 501-505, vol. 35.

Jakes et al., "Identification of 3- and 4-repeat Tau Isoforms within the PHF in Alzheimer's Disease," The EMBO Journal, 1991, pp. 2725-2729, vol. 10, No. 10.

Janciauskiene et al., "In vitro amyloid fibril formulation from (1-antitrypsin," Bio Chem, 1995, vol. 375, pp. 103-109.

Kaech et al., "Cytoskeletal Plasticity in Cells Expressing Neuronal Microtubule-Associated Proteins," Neuron, Dec. 1996, pp. 1189-1199, vol. 17.

Kiese et al., "Comparative studies on the effects of toluidine blue and methylene blue on the reduction of ferrihaemoglobin in man and dog", Europ. J. Clin. Pharmacol., 1972, vol. 4, pp. 115-118.

Klymkowsky, "Weaving a tangled web: the interconnected cytoskeleton", Nature Cell Biology (1999) vol. 1, No. 5, p. E121.

KOHLER & CO., "Toluidinblau," Drug Information, Alsbach, Germany, Jul. 1997.

KOHLER & CO., "Toluidinblau," Drug Information, Alsbach, Germany.

Koryta "Ions, Electrodes and Membranes", Institute of Physiology, Second Edition, John Wiley & Sons (1991).

Ksiezak-Reding et al., "Mass and Physical Dimensions of Two Distinct Populations of Paired Helical Filaments," Neurobiology of Aging, 1993, pp. 11-18, vol. 15, No. 1.

Ksiezak-Reding et al., "Structural Stability of Paired Helical Filaments Reguires Microtubule-Binding Domains of Tau: A Model for Self-Association," Neuron, 1991, pp. 717-728, vol. 6.

Ksiezak-Reding, et al. Assembled tau filaments differ from native paired helical filaments as determined by scanning transmission electron microscopy (STEM), Brain Research (1998), vol. 814, pp. 86-98.

Lai et al., "Examination of Phosphorylated Tau Protein as a PHF-Precursor at Early State Alzheimer's Disease," Neurobiology of Aging, 1995, pp. 433-445, vol. 16, No. 3.

Lai R., The Role of Abnormal Phosphorylation of Tau Protein in the Development of Neurofibrillary Pathology in Alzheimer's Disease, pp. 1-243.

Lai R., "The Role of Abnormal Phosphorylation of Tau Protein in the Development of Neurofibrillary Pathology in Alzheimer's Disease"—Submitted for the Degree of Doctor of Philosophy at the University of Cambridge, 1994, pp. 1-243.

Ledesma et al., "Implication of brain cdc2 and MAP2 kinases in the phosphorylation of tau protein in Alzheimer's disease," FEBS, 1992, vol. 308, No. 2, pp. 218-224.

Lee et al., "Tau Proteins and their significance in the Pathobiology of Alzheimer's Disease," Pathobiology of Alzheimer's Disease, 1995, pp. 41-58.

Lee et al., "Tau Proteins and their significance in the Pathobiology of Alzheimer's Disease," Pathobiology of Alzheimer's Disease, pp. 41-58.

Lee et al., untitled, Science, 1992., vol. 251.

Lee et al., "A68: A Major Subunit of Paired Helical Filaments and Derivatized Forms of Normal Tau," Science, 1991, pp. 675-678, vol. 251.

Lewis, et al. "Microtubule-Associated Protein MAP2 Shares a Microtubule Binding Motif with Tau Protein", Science(Nov. 11, 1988) vol. 242, pp. 936-939.

Lichtenberg-Kraag, et al. "Alzheimer-Type Phosphorylation of Microtubule-Associated Protein Tau In Vitro", 1991/92.

Lichtenberg-Kraag, et al. "Phosphorylation-dependent epitopes of neurofilament antibodies on tau protein and relationship with Alzheimer tau", Proc. Natl. Acad. Sci (Jun. 1992) vol. 89, pp. 5384-5388.

Link, E. "Targeting Melanoma with 211 At/131I-Methylene Blue: Preclinical and Clinical Experience", Hybridoma (Nov. 1, 1999), vol. 18, No. 1, pp. 77-82.

Lomas, et al. "The mechanism of Z alpha1-antitrypsin accumulation in the liver", Letters of Nature (Jun. 18, 1992), vol. 357, pp. 605-607.

Makaetova-Ladinska, et al. "Staging of cytoskeletal and beta-amyloid changes in human isocortex reveals biphasic synaptic protein response during progression of Alzheimer's disease", American Journal of Pathology (Aug. 2000) vol. 157, No. 2, pp. 623-636.

Martinez et al., "Methylene blue alterse retention of inhibitory avoidance responses", Physiol. Psychol., 1978, vol. 6(63), pp. 387-390.

Mashberg A., "Tolonium (Toluidine blue) rinse—a screening method for recognition of squanous carcinoma—continuing study of oral-cancer 4," Jama-Journal of the American Medical Association, vol. 245, No. 23, 1981, pp. 2408-2410.

Mashberg A., "Tolonium (Toluidine blue) rinse—a screening method for recognition of squanous carcinoma—continuing study of oral-cancer 4," Jama-Journal of the American Medical Association, vol. 245, No. 23, pp. 2408-2410.

(56) References Cited

OTHER PUBLICATIONS

Masuda, M., et al., Small molecule inhibitors of (-synuclein filament assembly. Biochemistry, (2006), pp. 6085-6094, 45.
May et al., "Reduction and uptake of methylene blue by human erythrocytes", Am J Physiol Cell Physiol, 286, 2004, pp. C390-C1398.
Mena et al., "A Progressive Depsotion of Paired Helical Filaments (PHF) in the Brain Characterizes the Evolution of Dementia in Alzheimer's Disease," Journal of Neuropathology and Experimental Neurology, 1991, pp. 474-490.
Mena et al., "Monitoring Pathological Assembly of tau and (-Amyloid Proteins in Alzheimer's Disease," Acta Neuropathol., 1994, pp. 50-56.
Mena et al., "Staging the Pathological Assembly of Truncated tau Protein into Paired Helical Filaments in Alzheimer's Disease," Acta Neuropathol, 1995, pp. 633-641.
Muller T., "Light-microscopic demonstration of methylene blue accumulation sites in mouse brain after supravital staining", Acta Anat., 1992, vol. 144, pp. 39-44.
Murphy et al., "Cyclic-voltametric studies of some phenothiazine dyes," J. Chem. Soc., Faraday Trans., 1984, vol. 80, pp. 2745-2750.
Novak et al., "Molecular Characterization of the Minimal Protease Resistant Tau Unit of the Alzheimer's Disease Paired Helical Filament," The EMBO Journal, 1993, pp. 365-370, vol. 12, No. 1.
Pedrotti et al., Biochemistry, 1994, pp. 8798-8806, vol. 33.
Perez et al., "In vitro assembly of tau protein: Mapping the regions involved in filament formation," Biochemistry, 2001, vol. 40, 5983-5991.
Perez-Tur et al., "Neurodegenerative disease of Guam: Analysis of TAU," American Academy of Neurology, 1999, vol. 53, pp. 411-412.
Pickhardt et al., "Anthraquinones inhibit tau aggregation and dissolve Alzheimer paired helical filaments in vitro and in cells," Journal of Biological Chemistry, 2005, vol. 280, pp. 3628-3635.
Poulter et al., "Locations and immunoreactivities of phosphorylation sites on bovine and porcine tau proteins and a PHF-tau fragment," The Journal of Biological Chemistry, 1993, vol. 268, No. 13, pp. 9636-9644.
Rumbolz et al., "Use of protamine sulfate and toluidine blue for abnormal uterine bleeding," Am. J. Obst. & Gynec., May 1952, vol. 63, No. 5, pp. 1029-1037.
Sato-Harada et al., "Microtubule-associated Proteins Regulate Microtubule Function as the Track for Intracellular Membrane Organelle Transports," Cell Structure and Function, 1996, pp. 283-295, vol. 21.
Schneider et al., "Phosphorylation that detaches tau protein from microtubules (Ser262, Ser214) also protects it against aggregation into Alzheimer paired helical filaments," Biochemistry, 1999, vol. 38, pp. 3549-3558.
Shojania, A.M. et al., "The effect of toluidine blue and methylene blue in immunochemical reactions in vitro", Clinical Immunology and Immunopathology, (1987), pp. 223-228, 43.
Sigma Biosciences, "In vitro toxicology assay kit lactate dehydrogenase based," Cell Viability (2009).
Smith et al., "The molecular pathology of Alzheimer's disease: are we any closer to understanding the neurodegenerative process?," Neuropathology and Applied Neurobiology, 1994, p. 322 338, vol. 20, XP002002176.
Taniguchi et al, "Inhibition of heparin-induced tau filament formation by phenothiazines, polyphenols, and porphyrins." JBC Papers in Press, 2004, Manuscript M408714200.
Tint et al., "Acute Inactivation of Tau Has No Effect on Dynamics of Microtubules in Growing Axons of Cultured Sympathetic Neurons," The Journal of Neuroscience, Nov. 1, 1998, pp. 8661-8673, vol. 18, No. 21.
Van Rossum et al., "Cytoskeletal Dynamics in Dendritic Spines: Direct Modulation by Glutamate Receptors?," Trends Neurosci., 1992, pp. 290-295, vol. 22.
Varani et al., "Structure of tau exon 10 splicing regulatory element RNA and destabilization by mutations of frontotemporal dementia and parkinsonism linked to chromosome 17," Proc. Natl. Acad. Sci. USA, 1999, vol. 96, pp. 8229-8234.
Vippagunta et al, Crystalline Solids, Advance Drug Delivery Reviews (2001), 48:3-26.
Von Bergen et al., "Assembly of tau protein into Alzheimer's paired helical filaments depends on a local sequence motif forming beta structure," Proceedings of the National Academy of Sciences of USA, National Academy of Science, May 9, 2000, vol. 97, No. 10, pp. 5129-5134.
Wille et al., Alzheimer-like paired helical filaments and antiparallel dimars formed from microtubule-associated protein tau in vitro, J. Cell Biol., 1992, pp. 573-584, vol. 118.
Wischik C., "Molecular Neuropathology of Alzheimer's Disease," 1989, pp. 44-70.
Wischik C., "Molecular neuropathology of Alzheimer's disease," John Libbey & Co., 1991, pp. 239-250.
Wischik et al. "Quantitative Analysis of Tau Protein in Paired Helical Filament Preparations: Implications for the Role of Tau Protein Phosphorylation in PHE Assembly in Alzheimer's Disease," Neurobiology of Aging, 1995, pp. 409-431, vol. 16, No. 3.
Wischik et al., "Author's Response to Commentaries," pp. 423-431 (no date available).
Wischik et al., "Isolation of a Fragment of Tau Derived From the Core of the Paired Helical Filament of Alzheimer Disease," Proc. Natl. Acad. Sol. USA, Jun. 1998, pp. 4506-4510, vol. 85.
Wischik et al., "Modelling Prior-like Processing of Tau Protein in Alzheimer's disease for Pharmaceutical Development," Harwood Acad. Publishers, 1997, pp. 185-241.
Wischik et al., "Selective inhibition of Alzheimer disease-like tau aggregation by phenothiazines," Proc. Natl. Acad. Sci. USA, 1996, p. 11213-11218, vol. 93.
Wischik et al., "Structural Characterization of the Core of the Paired Helical Filament of Alzheimer Disease," Proc. Natl. Acad. Sci. USA, Jul. 1998, p. 4884 4888, vol. 85.
Wischik et al., "Structure, Biochemistry and Molecular Pathogenesis of Paired Helical Filaments in Alzheimer's Disease," Pathobiology of Alzheimer's Disease, 1995, pp. 10-39.
Wischik et al., "Subunit Structure of Paired Helical Filaments in Alzheimer's Disease," The Journal of Cell Biology, 1985, p. 1905-1913.
Wischik et al., "Quantitative Analysis of Tau Protein in Paired Helical Filament Preparations: Implications for the Role of Tau Protein Phosphorylation in PHF Assembly in Alzheimer's Disease," Neurobiology of Aging, 1995, pp. 409-431, vol. 16, No. 3.
Wischik et al., "The molecular basis of tau protein pathology in Alzheimer's disease and related neurodegenerative dementias," In Neurobiology of Alzheimer's Disease (Eds. D. Dawbarn & S.J. Allen) Oxford University Press, Oxford, 2001, pp. 103-206.
Wischik et al., "The molecular basis of tau protein pathology in Alzheimer's disease and related neurodegenerative dementias," In Neurobiology of Alzheimer's Disease (Eds. D. Dawbarn & S.J. Allen) Oxford University Press, Oxford, pp. 103-206.
Wischik, "The Structure and Biochemisty of Paired Helical Filaments in Alzheimer's Disease", Dissertation/Thesis—May 19, 1989, pp. 182, 189, 232-234.
Wischik, "Cell biology of the Alzheimer tangle," Current Opinion in Cell Biology, 1989, vol. 1, pp. 115-122.
Wischik, et al. "The role of tau protein in the neurodegenerative dementias", Dementia 2nd Edition (2000), Hodder Arnold Published, pp. 461-492.
Yen et al., "Alzheimer's Neurofibrillary Tangles Contain Unique Epitopes and Epitopes in Common With the Heat-Stable Microtubule Associated Proteins Tau and MAP2," AJP, Jan. 1987, vol. 126.
Zhang, et al., "Methylene Blue Prevents Neurodegeneration Caused by Rotenone in the Retina", Neurotoxicity Research, vol. 9, No. 1, 2006, pp. 47-57.
Berge et al.; "Pharmaceutical Salts"; Journal of Pharmaceutical Sciences, 66(1):1-19 (Jan. 1977).
Non-Final Office Action for U.S. Appl. No. 15/056,610 dated Feb. 2, 2017.
U.S. Final Office Action issued in U.S. Appl. No. 14/866,035 dated Dec. 13, 2016.

(56) References Cited

OTHER PUBLICATIONS

Claims examined in Notification of Reexamination for CN Application No. 201510002365.2.
Decision of Final Rejection for CN Application No. 201510002365.2, dated Dec. 18, 2018.
Notification of Reexamination for CN Application No. 201510002365.2, dated Dec. 19, 2019.
Baxman et al, Effect of Vitamin C Supplements on Urinary Oxalate and pH in Calcium Stone-forming Patients. Kidney International. 2003; 63(3):1066-1071.
Black et al., Structure, Solubility, Screening, and Synthesis of Molecular Salts. J Pharm Sci. May 2007;96(5):1053-68. doi: 10.1002/jps.20927.
Contineanu et al., Radiolysis of Methylene Blue Studied by ESR. Radiochem. Radioanal. Letters. 1983; 57(1): 9-22.
Drew et al., Derivatives of Methylene-blue. Journal of the Chemical Society. 1933:248-253.
Han et al., Medicament Manufacture Technology. Mar. 2000. First Edition. Chapter 1. Science and Technology Literature Press, Eds. pp. 215-216.
Higson et al., Iron enhancement of ascorbate toxicity. Free Radic Res Commun. 1988;5(2):107-15. doi: 10.3109/10715768809066918.
Mayo Clinic staff, Alzheimer's prevention: Does it exist? Aug. 31, 2010. Retrieved from http://www.mayoclinic.com/health/alzheimersprevention/AN02099/METHOD=print on Sep. 25, 2012.
Murthy et al., Cyclic-voltametric studies of some phenothiazine dyes. J. Chem. Soc., Faraday Transactions 1. 1984;80:2745-2750.
Raust et al., Stability studies of ionised and non-ionised 3,4-diaminopyridine: Hypothesis of degradation pathways and chemical structure of degradation products. Journal of Pharmaceutical and Biomedical Analysis. 2007;43:83-88.
Schwab et al, A Protein Aggregation Inhibitor, Leuco-Methylthioninium Bis(Hydromethanesulfonate), Decreases α-Synuclein Inclusions in a Transgenic Mouse Model of Synucleinopathy. Frontiers in Molecular Neuroscience. Jan. 2018; 10(447):1-15.
Shiyu, Synthetic drugs and intermediates Manual. 2003. Chapter 4. Beijing Chemical Industry Press, Eds. p. 285.
Shumin, Medicinal Chemistry. 2014. Shandong People's Publishing House, Eds.
Sigfridsson et al., A case study where pharmaceutical salts were used to address the issue of low in vivo exposure. Drug Development and Industrial Pharmacy. 2019;45(2):202-211. DOI 10.1080/03639045.2018.1529184.
Solomons, Organic Chemistry. 1984. 3rd Edition. John Wiley & Sons Inc., Eds. pp. 62 and 850.
Wischik, The Structure and Biochemistry of Paired Helical Filaments in Alzheimer's Disease, Part I and II. Thesis for Cambridge University. May 1989. pp. 1-455.
Wood et al., Protein aggregation in motor neurone disorders. Neuropathology and Applied Neurobiology. 2003;29:529-545.
Yale et al., 4-{3-[10-(2-Trifluoromethyl)-phenothiazinyl]-propyl}-1-piperazine-ethanol[1] and Related Compounds. Squibb Institute for Medical Research. Apr. 20, 1960;82: 2039-2042.
Non-Final Office Action on U.S. Appl. No. 16/248,746 dated Mar. 20, 2019 (including U.S. Pat. No. 6,068,854A; U.S. Pat. No. 6,376,205B1; U.S. Pat. No. 7,737,138B2; U.S. Pat. No. 9,211,294B2; U.S. Pat. No. 10,188,658B2; US2004/0078835A1; WO2006/091728A2).

\* cited by examiner

3,7-DIAMINO-10H-PHENOTHIAZINE SALTS AND THEIR USE

CROSS-REFERENCE TO RELATED PATENT APPLICATIONS

This application is a Divisional of U.S. application Ser. No. 14/248,730, filed Apr. 9, 2014, which is a Continuation of U.S. application Ser. No. 13/011,797, filed Jan. 21, 2011, now U.S. Pat. No. 8,710,051, which is a Continuation of U.S. application Ser. No. 12/294,599 filed Sep. 25, 2008, (National Stage of PCT/GB2007/001103), now U.S. Pat. No. 7,888,350, which claims priority from Provisional U.S. Application 60/786,690, filed Mar. 29, 2006. All of the aforesaid applications are incorporated herein by reference in their entirety.

BACKGROUND OF THE INVENTION

1. Technical Field

This invention pertains generally to the field of phenothiazine compounds, and more particularly to certain stably reduced phenothiazine compounds, specifically, certain 3,7-diamino-10H-phenothiazine (DAPTZ) compounds, for example, N,N,N',N'-tetramethyl-10H-phenothiazine-3,7-diamine bis(hydrogen chloride) and N,N,N',N'-tetramethyl-10H-phenothiazine-3,7-diamine bis(hydrogen iodide). These compounds are useful as drugs, for example, in the treatment of tauopathies, such as Alzheimer's disease, and also as prodrugs for the corresponding oxidized thioninium drugs (for example, methythioninium chloride, MTC).

2. Background

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Conditions of dementia are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska, E. B. et al., 2000, Am. J. Pathol., Vol. 157, No. 2, pp. 623-636). Methythioninium chloride (MTC) and other diaminophenothiazines have been described as inhibitors of protein aggregation in such diseases, that is, diseases in which proteins aggregate pathologically (see, for example, WO 96/30766 and WO 02/055720).

Methythioninium chloride (MTC) is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria either singly (see, e.g., Guttmann, P. and Ehrlich, P., 1891, "Uber die wirkung des methylenblau bei malaria," Berl. Klin. Woschenr., Vol. 28, pp. 953-956) or in combination with chloroquine (see, e.g., Schirmer, H., et al., 2003, "Methylene blue as an antimalarial agent," Redox Report, Vol. 8, pp. 272-275; Rengelshausen, J., et al., 2004, "Pharmacokinetic interaction of chloroquine and methylene blue combination against malaria," European Journal of Clinical Pharmacology, Vol. 60, pp. 709-715). Malaria in humans is caused by one of four protozoan species of the genus *Plasmodium: P. falciparum, P. vivax, P. ovale,* or *P. malariae.* All species are transmitted by the bite of an infected female *Anopheles* mosquito. Occasionally, transmission occurs by blood transfusion, organ transplantation, needle-sharing, or congenitally from mother to fetus. Malaria causes 300-500 million infections worldwide and approximately 1 million deaths annually. Drug resistance, however, is a major concern and is greatest for *P. falciparum*, the species that accounts for almost all malaria-related deaths. Drugs or drug combinations that are currently recommended for prophylaxis of malaria include chloroquine/proguanil hydrochloride, mefloquine, doxycycline, and primaquine.

MTC (under the name Virostat®, from Bioenvision Inc., New York) has shown potent viricidal activity in vitro. Specifically Virostat® is effective against viruses such as HIV and West Nile Virus in laboratory tests. West Nile virus (WNV) is a potentially serious illness affecting the central nervous system. The large majority of infected people will show no visible symptoms or mild flu-like symptoms such as fever and headache. About one in 150 will develop severe symptoms including tremors, convulsions, muscle weakness, vision loss, numbness, paralysis, or coma. Generally, WNV is spread by the bite of an infected mosquito, but can also spread through blood transfusions, organ transplants, breastfeeding or during pregnancy from mother to child.

Virostat® is also currently in clinical trials for the treatment of chronic Hepatitis C. Hepatitis C is a viral infection of the liver. The virus, HCV, is a major cause of acute hepatitis and chronic liver disease, including cirrhosis and liver cancer. HCV is spread primarily by direct contact with human blood. The major causes of HCV infection worldwide are use of unscreened blood transfusions, and re-use of needles and syringes that have not been adequately sterilized. The World Health Organization has declared hepatitis C a global health problem, with approximately 3% of the world's population infected with HCV and it varies considerably by region. The prevalence in the US is estimated at 1.3% or approximately 3.5 million people. Egypt has a population of approximately 62 million and contains the highest prevalence of hepatitis C in the world, estimated at over 20% of the nation's approximately 62 million people.

MTC, when combined with light, can prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compound then binds to the nucleic acid of the viral or bacterial pathogen, preventing replication of the DNA or RNA. Because MTC can inactivate pathogens, it has the potential to reduce the risk of transmission of pathogens that would remain undetected by testing.

Oral and parenteral formulations of MTC are commercially available in the United States, usually under the name Urolene Blue®.

SUMMARY OF THE INVENTION

One aspect of the invention pertains to certain compounds, specifically, certain 3,7-diamino-10H-phenothiazine (DAPTZ) compounds, as described herein.

Another aspect of the invention pertains to a composition comprising a DAPTZ compound as described herein and a pharmaceutically acceptable carrier or diluent.

Another aspect of the invention pertains to a pharmaceutical composition comprising a DAPTZ compound as described herein and a pharmaceutically acceptable carrier or diluent.

Another aspect of the invention pertains to a method of preparing a pharmaceutical composition comprising admixing a DAPTZ compound as described herein and a pharmaceutically acceptable carrier or diluent.

Another aspect of the present invention pertains to a method of reversing and/or inhibiting the aggregation of a protein (e.g., a tau protein, a synuclein, etc.), for example, aggregation of a protein associated with a neurodegenerative disease and/or clinical dementia, comprising contacting the protein with an effective amount of a DAPTZ compound, as described herein. Such a method may be performed in vitro, or in vivo.

Another aspect of the present invention pertains to a method of treatment or prophylaxis of a disease condition in a subject comprising administering to said subject a prophylactically or therapeutically effective amount of a DAPTZ compound, as described herein, preferably in the form of a pharmaceutical composition.

Another aspect of the present invention pertains to a DAPTZ compound as described herein for use in a method of treatment or prophylaxis (e.g., of a disease condition) of the human or animal body by therapy.

Another aspect of the present invention pertains to use of a DAPTZ compound, as described herein, in the manufacture of a medicament for use in the treatment or prophylaxis of a disease condition.

In one embodiment, the disease condition is a disease of protein aggregation.

In one embodiment, the disease condition is a tauopathy, e.g., a neurodegenerative tauopathy, e.g., Alzheimer's disease.

In one embodiment, the disease condition is skin cancer, e.g., melanoma.

In one embodiment, the disease condition is a viral, bacterial or protozoal disease condition, e.g., Hepatitis C, HIV, West Nile Virus (WNV), or malaria.

Another aspect of the present invention pertains to a method of inactivating a pathogen in a sample (for example a blood or plasma sample), comprising the steps of introducing a DAPTZ compound, as described herein, into the sample, and then exposing the sample to light.

Another aspect of the present invention pertains to a kit comprising (a) a DAPTZ compound as described herein, preferably provided as a pharmaceutical composition and in a suitable container and/or with suitable packaging; and (b) instructions for use, for example, written instructions on how to administer the compound.

As will be appreciated by one of skill in the art, features and preferred embodiments of one aspect of the invention will also pertain to other aspect of the invention.

BRIEF DESCRIPTION OF THE DRAWINGS

FIG. 1 is a . . . .

DETAILED DESCRIPTION OF THE PREFERRED EMBODIMENTS

Figure 1:
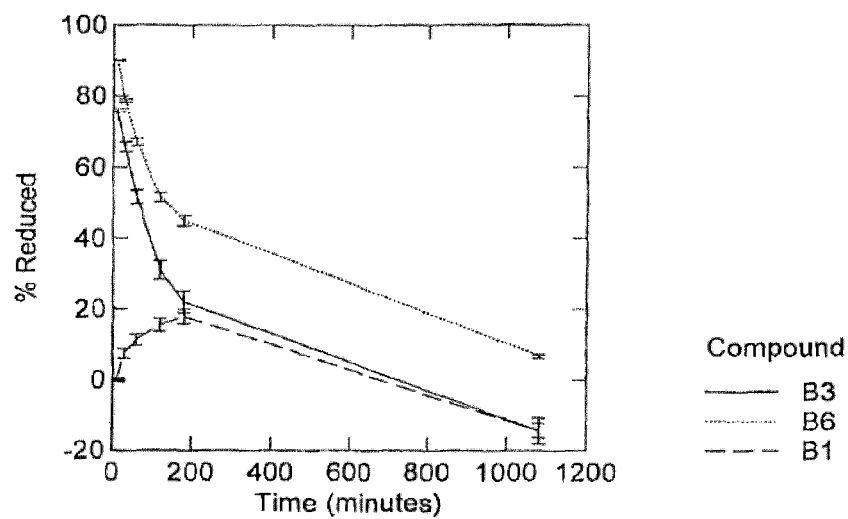
FIG. 1 is a graph of the percent reduced form (%) versus time (minutes) for each of three compounds, B1 (MTC), B3 (N,N,N',N'-Tetramethyl-10H-phenothiazine-3,7-diamine bis (hydrogen chloride)), and B6 (N,N,N',N'-Tetramethyl-10H-phenothiazine-3,7-diamine bis(hydrogen iodide)), as determined using absorbance at 665 nm.

Methythioninium Chloride (MTC) (also known as Methylene blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

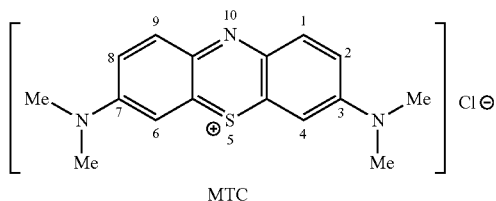

MTC

Methythioninium Chloride (MTC) (also known as Methylene Blue), perhaps the most well known phenothiazine dye and redox indicator, has also been used as an optical probe of biophysical systems, as an intercalator in nanoporous materials, as a redox mediator, and in photoelectrochomic imaging.

MTC, a phenothiazin-5-ium salt, may conveniently be considered to be an "oxidized form" when considered in respect of the corresponding 10H-phenothiazine compound, N,N,N',N'-tetramethyl-10H-phenothiazine-3,7-diamine, which may conveniently be considered to be a "reduced form":

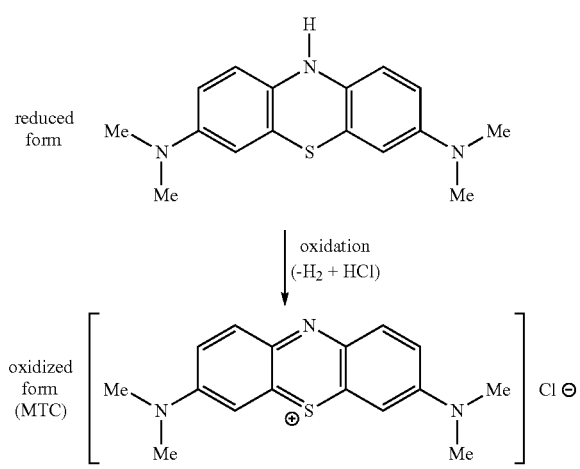

The "reduced form" (the "leuko form") is known to be unstable, and is readily and rapidly oxidized to give the corresponding "oxidized" form.

May et al. (Am J Physiol Cell Physiol, 2004, Vol. 286, pp. C1390-C1398) have shown that human erythrocytes sequentially reduce and take up MTC; that MTC itself is not taken up by the cells; that it is the reduced from of MTC that crosses the cell membrane; that the rate of uptake is enzyme dependent; and that both MTC and reduced MTC are concentrated in cells (reduced MTC re-equilibrates once inside the cell to form MTC).

MTC and similar drugs are taken up in the gut and enter the bloodstream. Unabsorbed drug percolates down the alimentary canal, to the distal gut. One important undesired side-effect is the effect of the unabsorbed drug in the distal gut, for example, sensitisation of the distal gut and/or antimicrobial effects of the unabsorbed drug on flora in the distal gut, both leading to diarrhoea. Therefore, it is desirable to minimize the amount of drug that percolates to the distal gut. By increasing the drug's update in the gut (i.e., by increasing the drug's bioavailability), dosage may be reduced, and the undesired side-effects, such as diarrhoea, may be ameliorated.

Since it is the reduced form of MTC that is taken up by cells, it would be desirable to administer the reduced form. This would also reduced reliance on the rate limiting step of enzymatic reduction.

The inventors have identified a class of compounds that may also be considered to be in the "reduced form" when considered in respect of MTC, and which are surprisingly and unexpectedly stable. The compounds may therefore be described as "stabilized reduced forms," for example, of MTC.

These compounds are themselves active as drugs, and may also serve as prodrugs, yielding, upon oxidation, the corresponding oxidized compounds (e.g., MTC), which are also active as drugs.

One representative member of this class of compounds is shown below.

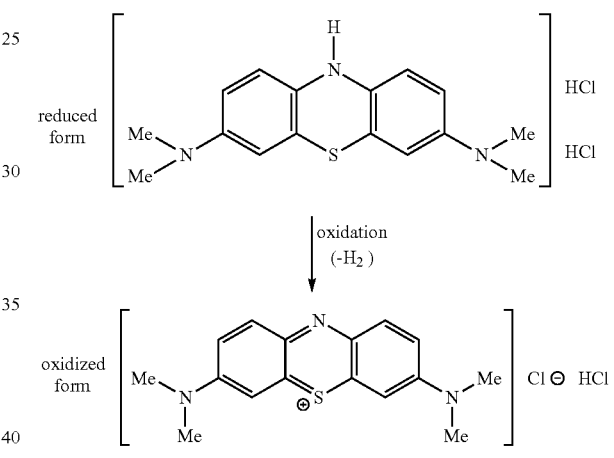

Another representative member of this class of compounds is shown below.

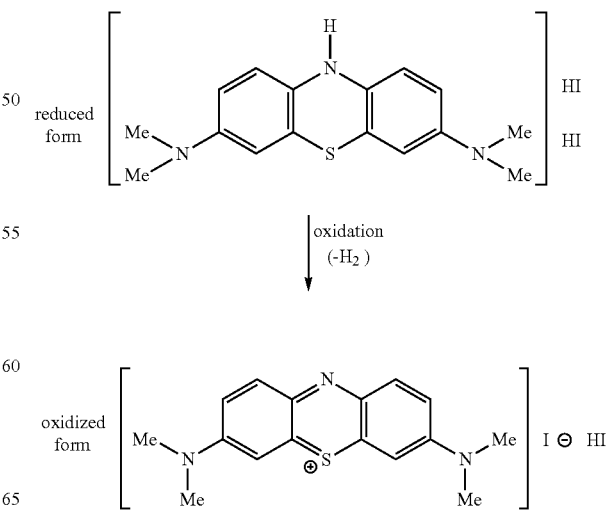

The Compounds

In general, the present invention pertains certain 3,7-diamino-10H-phenothiazine compounds of the following formula (collectively referred to herein as "diamino-phenothiazine compounds" and/or "DAPTZ compounds"):

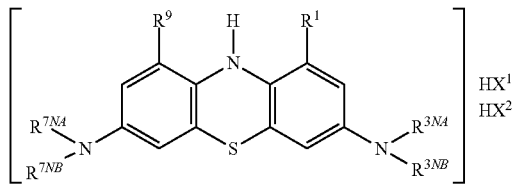

wherein:

each of $R^1$ and $R^9$ is independently selected from: —H, $C_{1-4}$alkyl, $C_{2-4}$alkenyl, and halogenated $C_{1-4}$alkyl;

each of $R^{3NA}$ and $R^{3NB}$ is independently selected from: —H, $C_{1-4}$alkyl, $C_{2-4}$alkenyl, and halogenated $C_{1-4}$alkyl;

each of $R^{7NA}$ and $R^{7NB}$ is independently selected from: —H, $C_{1-4}$alkyl, $C_{2-4}$alkenyl, and halogenated $C_{1-4}$alkyl;

each of $HX^1$ and $HX^2$ is independently a protic acid;

and pharmaceutically acceptable salts, solvates, and hydrates thereof.

Without wishing to be bound to any particular theory, the inventors believe that it is possible, if not likely, that the compounds exist in the following form:

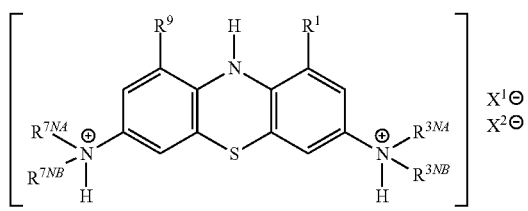

Although the DAPTZ compounds are themselves salts, they may also be provided in the form of a mixed salt (i.e., the DAPTZ in combination with another salt). Such mixed salts are intended to be encompassed by the term "and pharmaceutically acceptable salts thereof". Unless otherwise specified, a reference to a particular compound also includes salts thereof.

The DAPTZ compounds may also be provided in the form of a solvate or hydrate. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc. Unless otherwise specified, a reference to a particular compound also includes solvate forms thereof.

In one embodiment, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{2-4}$alkenyl groups, such as —CH=CH$_2$ (vinyl) and —CH$_2$—CH=CH$_2$ (allyl).

In one embodiment, the halogenated $C_{1-4}$alkyl groups are selected from: —CF$_3$, —CH$_2$CF$_3$, and —CF$_2$CF$_3$.

The Groups $R^1$ and $R^9$

In one embodiment, each of $R^1$ and $R^9$ is independently —H, -Me, -Et, or —CF$_3$.

In one embodiment, each of $R^1$ and $R^9$ is independently —H, -Me, or -Et.

In one embodiment, $R^1$ and $R^9$ are the same.

In one embodiment, $R^1$ and $R^9$ are different.

In one embodiment, each of $R^1$ and $R^9$ is independently —H.

In one embodiment, each of $R^1$ and $R^9$ is independently -Me.

In one embodiment, each of $R^1$ and $R^9$ is independently -Et.

The Groups $R^{3NA}$ and $R^{3NB}$

Each of $R^{3NA}$ and $R^{3NB}$ is independently selected from: —H, $C_{1-4}$alkyl, $C_{2-4}$alkenyl, and halogenated $C_{1-4}$alkyl.

In one embodiment, each of $R^{3NA}$ and $R^{3NB}$ is independently selected from: $C_{1-4}$alkyl, $C_{2-4}$alkenyl, and halogenated $C_{1-4}$alkyl.

In one embodiment, each of $R^{3NA}$ and $R^{3NB}$ is independently -Me, -Et, -nPr, -nBu, —CH$_2$—CH=CH$_2$, or —CF$_3$.

In one embodiment, each of $R^{3NA}$ and $R^{3NB}$ is independently -Me, -nPr, -nBu, —CH$_2$—CH=CH$_2$, or —CF$_3$.

In one embodiment, each of $R^{3NA}$ and $R^{3NB}$ is independently -Me or -Et.

In one embodiment, $R^{3NA}$ and $R^{3NB}$ are the same.

In one embodiment, $R^{3NA}$ and $R^{3NB}$ are different.

In one embodiment, each of $R^{3NA}$ and $R^{3NB}$ is independently -Me.

In one embodiment, each of $R^{3NA}$ and $R^{3NB}$ is independently -Et.

The Groups $R^{7NA}$ and $R^{7NB}$

Each of $R^{7NA}$ and $R^{7NB}$ is independently selected from: —H, $C_{1-4}$alkyl, $C_{2-4}$alkenyl, and halogenated $C_{1-4}$alkyl.

In one embodiment, each of $R^{7NA}$ and $R^{7NB}$ is independently selected from: $C_{1-4}$alkyl, $C_{2-4}$alkenyl, and halogenated $C_{1-4}$alkyl.

In one embodiment, each of $R^{7NA}$ and $R^{7NB}$ is independently -Me, -Et, -nPr, -nBu, —CH$_2$—CH=CH$_2$, or —CF$_3$.

In one embodiment, each of $R^{7NA}$ and $R^{7NB}$ is independently -Me, -nPr, -nBu, —CH$_2$—CH=CH$_2$, or —CF$_3$.

In one embodiment, each of $R^{7NA}$ and $R^{7NB}$ is independently -Me or -Et.

In one embodiment, $R^{7NA}$ and $R^{7NB}$ are the same.

In one embodiment, $R^{7NA}$ and $R^{7NB}$ are different.

In one embodiment, each of $R^{7NA}$ and $R^{7NB}$ is independently -Me.

In one embodiment, each of $R^{7NA}$ and $R^{7NB}$ is independently -Et.

In one embodiment, $R^{3NA}$ and $R^{3NB}$ and $R^{7NA}$ and $R^{7NB}$ are the same.

In one embodiment, $R^{3NA}$ and $R^{3NB}$ and $R^{7NA}$ and $R^{7NB}$ are as defined herein, with the proviso that at least one of $R^{3NA}$ and $R^{3NB}$ and $R^{7NA}$ and $R^{7NB}$ is other than -Et.

Optional Provisos

In one embodiment, the compound is as defined herein, but with the proviso that: $R^{3NA}$ and $R^{3NB}$ and $R^{7NA}$ and $R^{7NB}$ are not each -Et.

In one embodiment, the compound is as defined herein, but with the proviso that:
if: each of $R^1$ and $R^9$ is —H;
then: $R^{3NA}$ and $R^{3NB}$ and $R^{7NA}$ and $R^{7NB}$ are not each -Et.

The Groups —N($R^{3NA}$)($R^{3NB}$) and —N($R^{7NA}$)($R^{7NB}$)

In one embodiment:
each of $R^{3NA}$ and $R^{3NB}$ is independently $C_{1-4}$alkyl, $C_{2-4}$alkenyl, or halogenated $C_{1-4}$alkyl;
each of $R^{7NA}$ and $R^{7NB}$ is independently $C_{1-4}$alkyl, $C_{2-4}$alkenyl, or halogenated $C_{1-4}$alkyl;
optionally with the proviso that at least one of $R^{3NA}$ and $R^{3NB}$ and $R^{7NA}$ and $R^{7NB}$ is other than -Et.

In one embodiment:
each of $R^{3NA}$ and $R^{3NB}$ is independently -Me, -Et, -nPr, -nBu, —$CH_2$—CH=$CH_2$, or —$CF_3$;
each of $R^{7NA}$ and $R^{7NB}$ is independently -Me, -Et, -nPr, -nBu, —$CH_2$—CH=$CH_2$, or —$CF_3$;
optionally with the proviso that at least one of $R^{3NA}$ and $R^{3NB}$ and $R^{7NA}$ and $R^{7NB}$ is other than -Et.

In one embodiment:
each of $R^{3NA}$ and $R^{3NB}$ is independently -Me or -Et;
each of $R^{7NA}$ and $R^{7NB}$ is independently -Me or -Et;
optionally with the proviso that at least one of $R^{3NA}$ and $R^{3NB}$ and $R^{7NA}$ and $R^{7NB}$ is other than -Et.

In one embodiment, the groups —N($R^{3NA}$)($R^{3NB}$) and —N($R^{7NA}$)($R^{7NB}$) are the same.

In one embodiment, the groups —N($R^{3NA}$)($R^{3NB}$) and —N($R^{7NA}$)($R^{7NB}$) are different.

In one embodiment, each of the groups —N($R^{3NA}$)($R^{3NB}$) and —N($R^{7NA}$)($R^{7NB}$) is independently selected from: —$NMe_2$, —$NEt_2$, —N(nPr)$_2$, —N(Bu)$_2$, —NMeEt, —NMe(nPr), and —N($CH_2CH$=$CH_2$)$_2$.

In one embodiment, the groups —N($R^{3NA}$)($R^{3NB}$) and —N($R^{7NA}$)($R^{7NB}$) are the same, and are independently selected from: —$NMe_2$, —$NEt_2$, —N(nPr)$_2$, —N(Bu)$_2$, —NMeEt, —NMe(nPr), and —N($CH_2CH$=$CH_2$)$_2$.

In one embodiment, the groups —N($R^{3NA}$)($R^{3NB}$) and —N($R^{7NA}$)($R^{7NB}$) are the same, and are independently selected from: —$NMe_2$ and —$NEt_2$.

In one embodiment, each of the groups —N($R^{3NA}$)($R^{3NB}$) and —N($R^{7NA}$)($R^{7NB}$) is: —$NMe_2$+.

In one embodiment, at least one of the groups —N($R^{3NA}$)($R^{3NB}$) and —N($R^{7NA}$)($R^{7NB}$) is other than —$NEt_2$.

In one embodiment, each of the groups —N($R^{3NA}$)($R^{3NB}$) and —N($R^{7NA}$)($R^{7NB}$) is other than —$NEt_2$.

For example, in one embodiment, the groups —N($R^{3NA}$)($R^{3NB}$) and —N($R^{7NA}$)($R^{7NB}$) are the same, and are selected from: —$NMe_2$, —N(nPr)$_2$, —N(Bu)$_2$, —NMeEt, —NMe(nPr), and —N($CH_2CH$=$CH_2$)$_2$.

The Groups $HX^1$ and $HX^2$

Each of $HX^1$ and $HX^2$ is independently a protic acid.

Examples of protic acids include, for example, inorganic acids, such as hydrohalide acids (e.g., HCl, HBr, HI), nitric acid ($HNO_3$), sulphuric acid ($H_2SO_4$), and organic acids, such as carbonic acid ($H_2CO_3$) and acetic acid ($CH_3COOH$).

In one embodiment, each of $HX^1$ and $HX^2$ is independently a monoprotic acid.

In one embodiment, each of $HX^1$ and $HX^2$ is independently a hydrohalide acid (i.e., a hydrohalic acid)

In one embodiment, each of $HX^1$ and $HX^2$ is independently selected from HCl, HBr, and HI.

In one embodiment, $HX^1$ and $HX^2$ are the same.

In one embodiment, $HX^1$ and $HX^2$ are different.

In one embodiment, $HX^1$ and $HX^2$ are the same, and are independently selected from HCl, HBr, and HI. In this case, the compound (a diamino-phenothiazine compound) may conveniently be referred to as a "diamino-phenothiazine bis(hydrogen halide) salt".

In one embodiment, $HX^1$ and $HX^2$ are each HCl. In this case, the compound may conveniently be referred to as a "diamino-phenothiazine bis(hydrogen chloride) salt".

In one embodiment, $HX^1$ and $HX^2$ are each HBr. In this case, the compound may conveniently be referred to as a "diamino-phenothiazine bis(hydrogen bromide) salt".

In one embodiment, $HX^1$ and $HX^2$ are each HI. In this case, the compound may conveniently be referred to as a "diamino-phenothiazine bis(hydrogen iodide) salt".

Some Preferred Combinations

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —$NMe_2$ or —$NEt_2$.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —$NMe_2$.

In one embodiment:
each of $R^1$ and $R^9$ is independently —H; and
each of the groups —N($R^{3NA}$)($R^{3NB}$) and —N($R^{7NA}$)($R^{7NB}$) is independently —$NMe_2$ or —$NEt_2$.

In one embodiment:
each of $R^1$ and $R^9$ is independently —H; and
each of the groups —N($R^{3NA}$)($R^{3NB}$) and —N($R^{7NA}$)($R^{7NB}$) is independently —$NMe_2$.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —$NMe_2$ or —$NEt_2$; and
each of $HX^1$ and $HX^2$ is independently selected from HCl, HBr, and HI.

In one embodiment:
each of $R^1$ and $R^9$ is independently —H, -Me, or -Et; and
each of the groups —N($R^{3NA}$)($R^{3NB}$) and —N($R^{7NA}$)($R^{7NB}$) is independently —$NMe_2$; and each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —$NMe_2$ or —$NEt_2$; and
each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —$NMe_2$; and each of $HX^1$ and $HX^2$ is independently selected from HCl, HBr, and HI.

In one embodiment:
each of $R^1$ and $R^9$ is independently —H; and
each of the groups —N($R^{3NA}$)($R^{3NB}$) and —N($R^{7NA}$)($R^{7NB}$) is independently —$NMe_2$; and each of $HX^1$ and $HX^2$ is HCl.

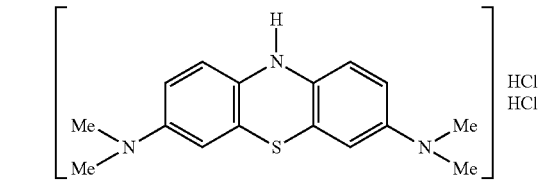

In one embodiment:

each of R¹ and R⁹ is independently —H; and each of the groups —N(R³ᴺᴬ)(R³ᴺᴮ) and —N(R⁷ᴺᴬ)(R⁷ᴺᴮ) is independently —NMe₂; and each of HX¹ and HX² is HBr.

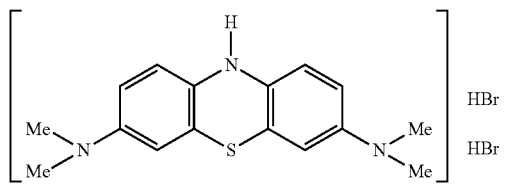

In one embodiment:

each of R¹ and R⁹ is independently —H; and each of the groups —N(R³ᴺᴬ)(R³ᴺᴮ) and —N(R⁷ᴺᴬ)(R⁷ᴺᴮ) is independently —NMe₂; and each of HX¹ and HX² is HI.

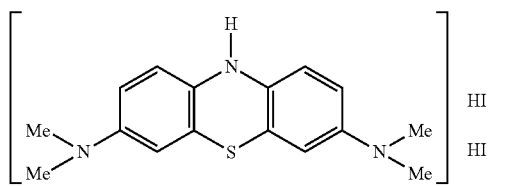

Isotopic Variation

In one embodiment, one or more of the carbon atoms of the compound is ¹¹C, ¹³C, or ¹⁴C.

In one embodiment, one or more of the carbon atoms of the compound is ¹¹C.

In one embodiment, one or more of the carbon atoms of the compound is ¹³C.

In one embodiment, one or more of the carbon atoms of the compound is ¹⁴C.

In one embodiment, one or more of the nitrogen atoms of the compound is ¹⁵N.

In one embodiment, one or more or all of the carbon atoms of one or more or all of the groups R³ᴺᴬ, R³ᴺᴮ, R⁷ᴺᴬ, R⁷ᴺᴮ, R¹, R⁹, and R¹⁰ is ¹¹C. (Or ¹³C.) (Or ¹⁴C.)

In one embodiment, one or more or all of the carbon atoms of one or more or all of the groups R³ᴺᴬ, R³ᴺᴮ, R⁷ᴺᴬ, and R⁷ᴺᴮ is ¹¹C. (Or ¹³C.) (Or ¹⁴C.)

In one embodiment, the groups —N(R³ᴺᴬ)(R³ᴺᴮ) and —N(R⁷ᴺᴬ)(R⁷ᴺᴮ) are the same, and are: —N(¹¹CH₃)₂. (Or —N(¹³CH₃)₂.) (Or —N(¹⁴CH₃)₂.)

Compatible Combinations

All compatible combinations of the embodiments described above are explicitly disclosed herein as if each combination was specifically and individually recited.

SOME PREFERRED EMBODIMENTS

In one embodiment, the compound is selected from the following compounds, and pharmaceutically acceptable salts, solvates, and hydrates thereof.

1

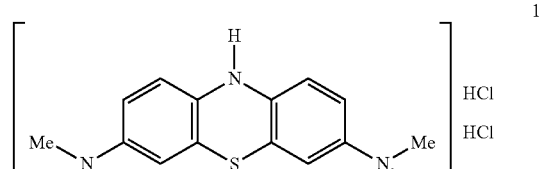

2

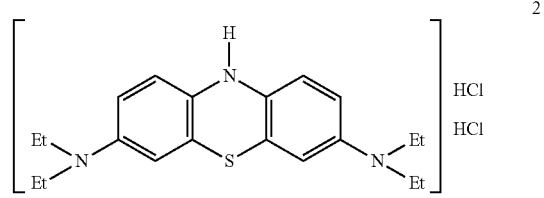

3

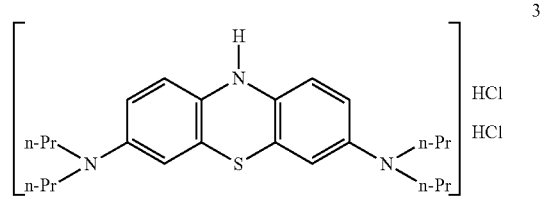

4

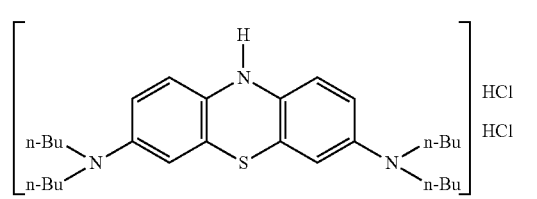

5

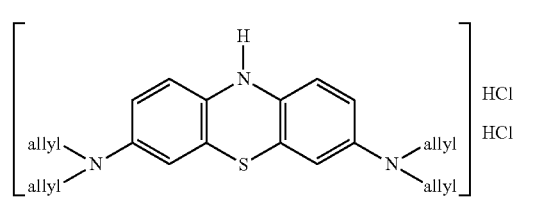

6

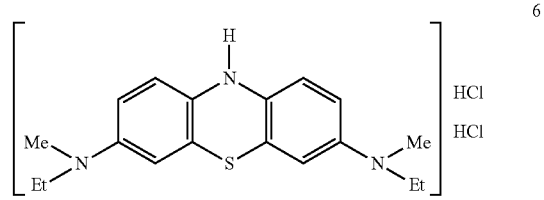

7

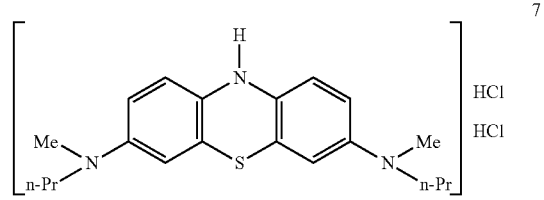

8

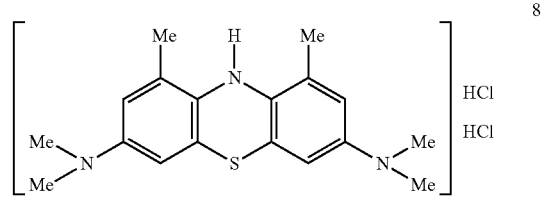

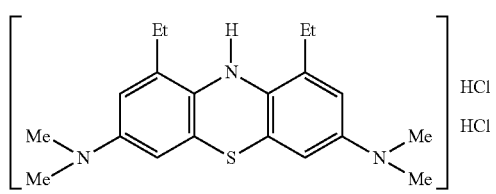
9
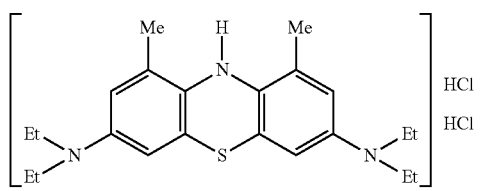
10
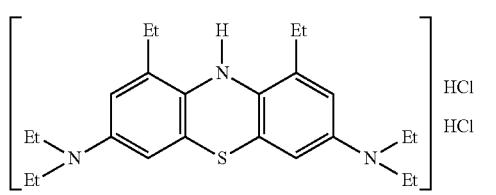
11
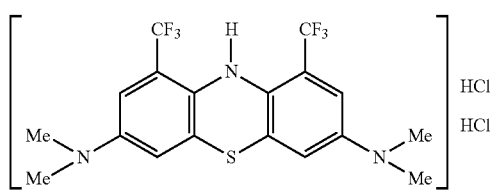
12
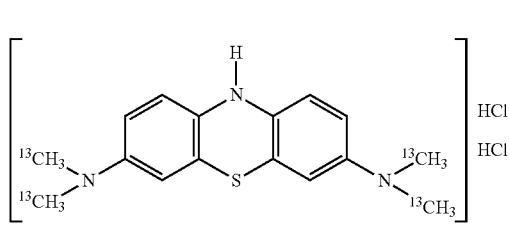
13
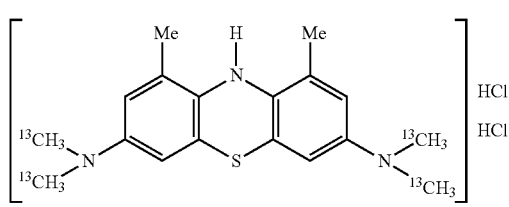
14
In one embodiment, the compound is selected from the following compounds, and pharmaceutically acceptable salts, solvates, and hydrates thereof.
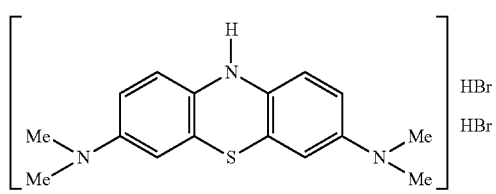
15
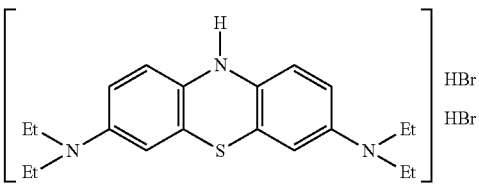
16
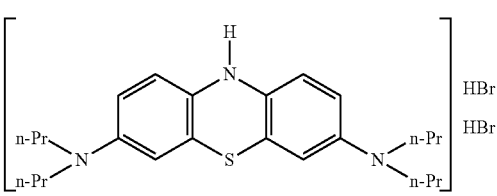
17
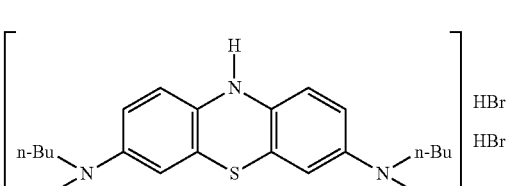
18
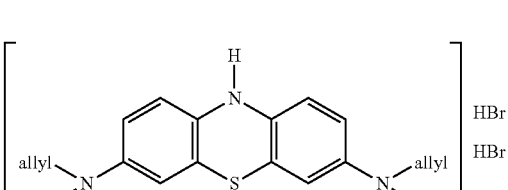
19
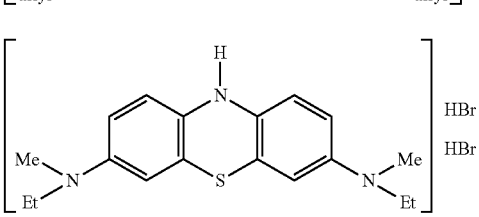
20
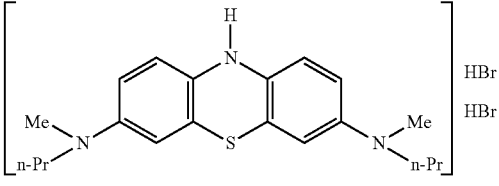
21
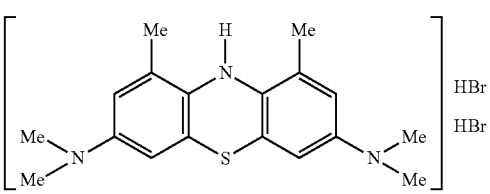
22
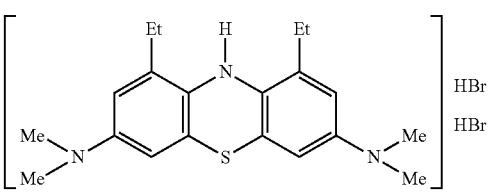
23

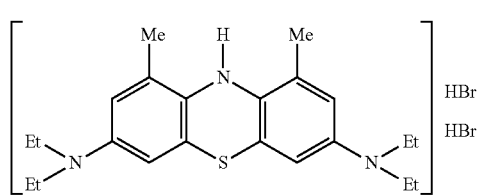
24
HBr
HBr
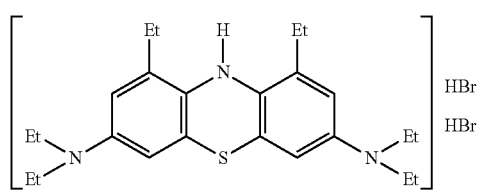
25
HBr
HBr
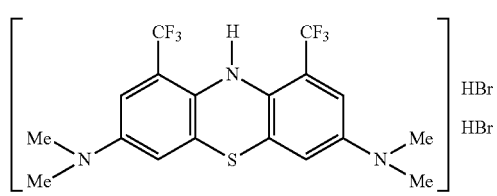
26
HBr
HBr
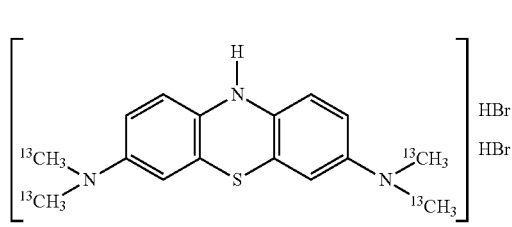
27
HBr
HBr
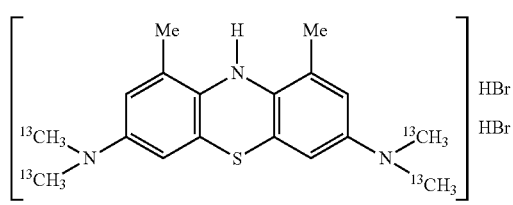
28
HBr
HBr
In one embodiment, the compound is selected from the following compounds, and pharmaceutically acceptable salts, solvates, and hydrates thereof.
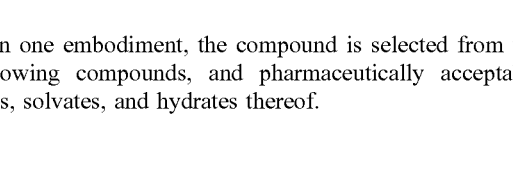
29
HI
HI
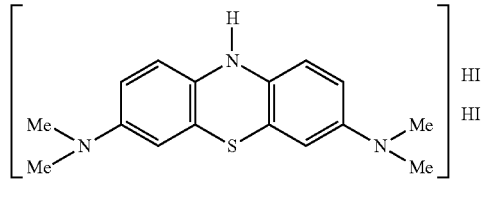
30
HI
HI
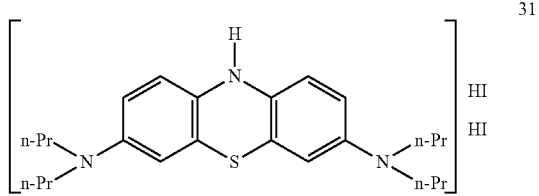
31
HI
HI
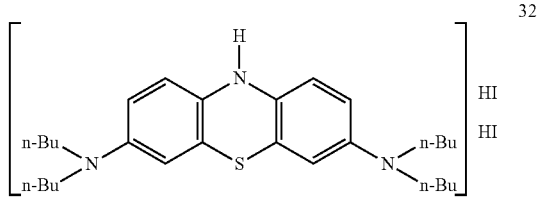
32
HI
HI
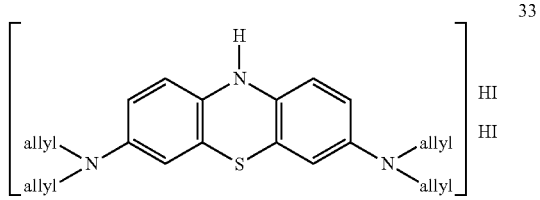
33
HI
HI
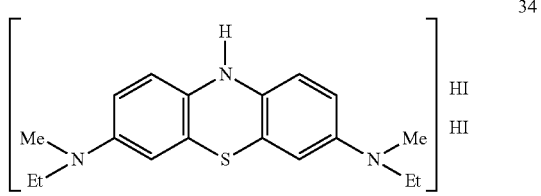
34
HI
HI
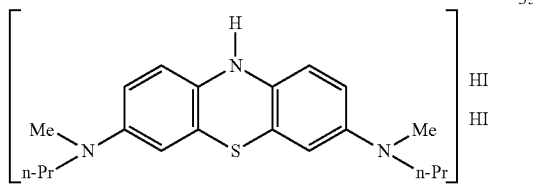
35
HI
HI
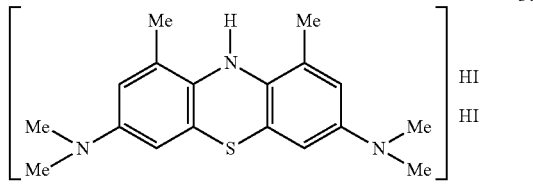
36
HI
HI
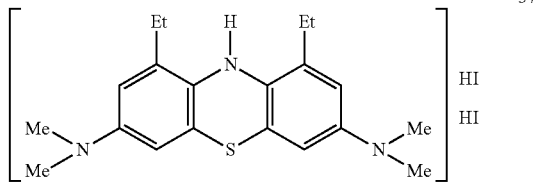
37
HI
HI
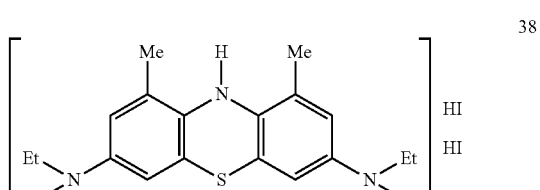
38
HI
HI

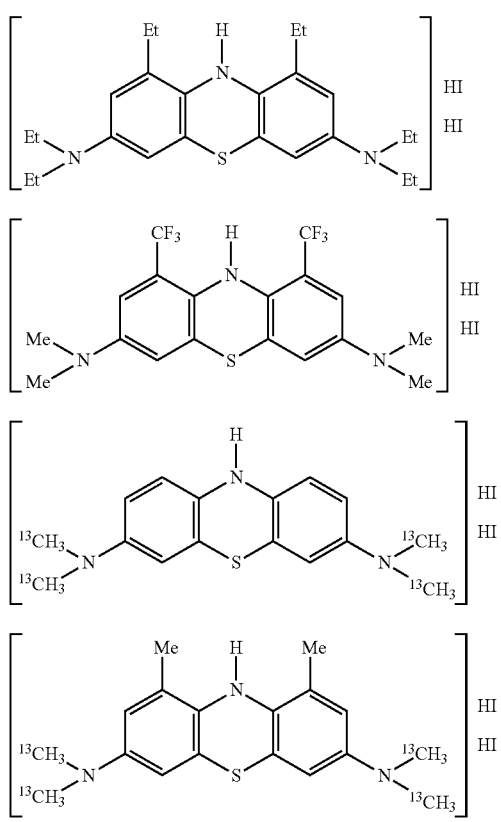

Purity

The DAPTZ compounds of the present invention may conveniently be described as being in a "stabilized reduced form". The compounds oxidize (e.g., autoxidize) to give the corresponding oxidized forms. Thus, it is likely, if not inevitable, that compositions comprising the DAPTZ compounds of the present invention will contain, as an impurity, as least some of the corresponding oxidized compound.

Thus, another aspect of the present invention pertains to DAPTZ compounds, as described herein, in substantially purified form and/or in a form substantially free from contaminants (e.g., the corresponding oxidized compound, other contaminants).

In one embodiment, the substantially purified form is at least 50% by weight pure, e.g., at least 60% by weight pure, e.g., at least 70% by weight pure, e.g., at least 80% by weight pure, e.g., at least 90% by weight pure, e.g., at least 95% by weight pure, e.g., at least 97% by weight pure, e.g., at least 98% by weight pure, e.g., at least 99% by weight pure.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Product-by-Process

In one embodiment, the DAPTZ compound is one which is obtained by, or is obtainable by, a method as described herein.

Chemical Synthesis

Methods for the chemical synthesis of DAPTZ compounds of the present invention are described herein. These and/or other well known methods may be modified and/or adapted in known ways in order to facilitate the synthesis of additional DAPTZ compounds within the scope of the present invention.

For example, a suitable phenothiazine may be converted to the corresponding 3,7-dinitro-phenothiazine, for example, using sodium nitrite with acetic acid and chloroform. The ring amino group may then be protected, for example, as the acetate, for example, using acetic anhydride and pyridine. The nitro groups may then be reduced to amino groups, for example, using tin (II) chloride with ethanol. The amino groups may then be substituted, for example, disubstituted, for example, methyl disubstituted, for example, using methyl iodide, sodium hydroxide, DMSO, and tetra-n-butyl ammonium bromide. The amino group may then be deprotected, for example, the N-acetyl group may be removed, for example, using concentrated aqueous hydrochloride acid. The corresponding salt is then prepared, for example, using concentrated aqueous hydrochloric acid, for example, at the same time as deprotection. An example of such a method is illustrated in the following scheme.

Scheme 1

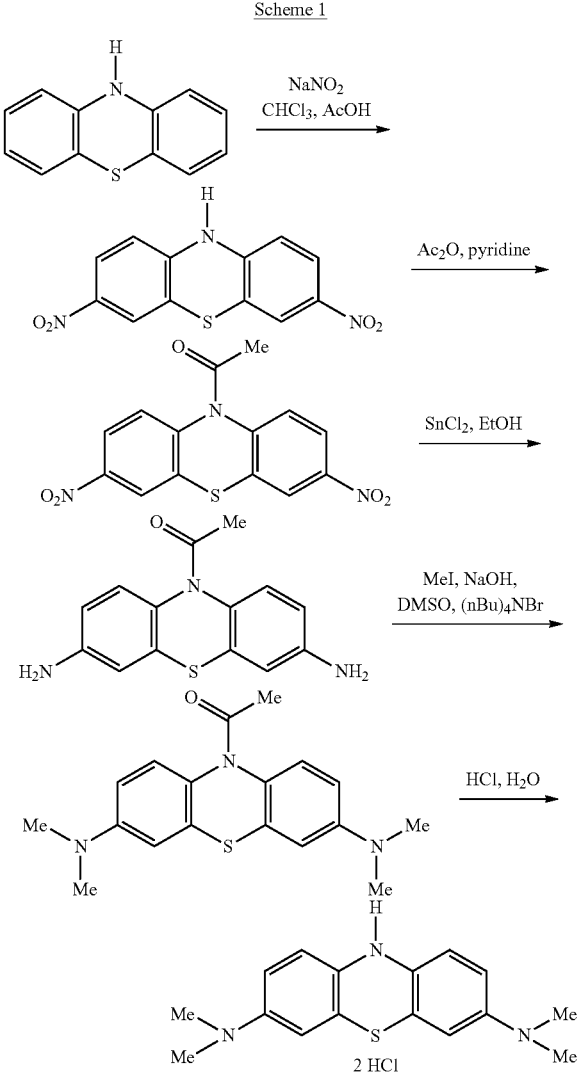

Thus, another aspect of the invention pertains to a method of preparing a 3,7-diamino-10H-phenothiazine (DAPTZ) compound of the following formula:

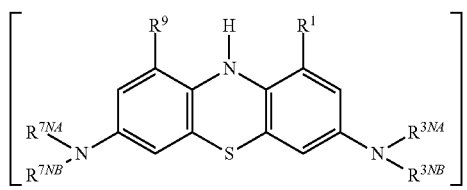

wherein $R^1$, $R^9$, $R^{3NA}$, $R^{3NB}$, $R^{7NA}$, $R^{7NB}$, $HX^1$ and $HX^2$ are as defined herein (for example,
where $HX^1$ and $HX^2$ are each HCl), comprising the step of:
(vi) salt formation (SF).
In one embodiment, the method comprises the steps of:
(v) ring amino deprotection (DP); and
(vi) salt formation (SF).
In one embodiment, the method comprises the steps of:
(iv) amine substitution (AS),
optional (v) ring amino deprotection (DP), and
(vi) salt formation (SF).
In one embodiment, the method comprises the steps of
(iii) nitro reduction (NR),
(iv) amine substitution (AS),
(v) ring amino deprotection (DP), and
(vi) salt formation (SF).
In one embodiment, the method comprises the steps of
optional (ii) ring amino protection (AP),
(iii) nitro reduction (NR),
(iv) amine substitution (AS),
(v) ring amino deprotection (DP), and
(vi) salt formation (SF).
In one embodiment, the method comprises the steps of
(i) nitration (NO),
(ii) ring amino protection (AP),
(iii) nitro reduction (NR),
(iv) amine substitution (AS),
(v) ring amino deprotection (DP), and
(vi) salt formation (SF).
In one embodiment, the steps are performed in the order listed (i.e., any step in the list is performed at the same time as, or subsequent to, the preceding step in the list).
In one embodiment, the step of (v) ring amino deprotection (DP) and the step of (vi) salt formation (SF) are performed simultaneously (i.e., as one step).
In one embodiment, the nitration (NO) step is:
(i) nitration (NO), wherein a 10H-phenothiazine is converted to a 3,7-dinitro-10H-phenothiazine, for example:

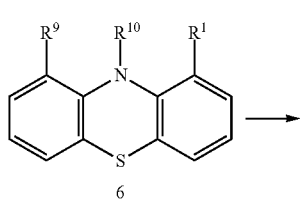

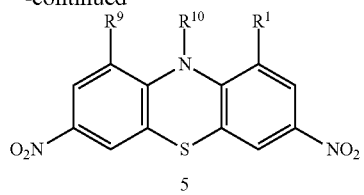

In one embodiment, nitration is performed using a nitrite, for example, sodium nitrite, for example, sodium nitrite with acetic acid and chloroform. In one embodiment, $R^{10}$ is —H.
In one embodiment, the ring amino protection (AP) step is:
(ii) ring amino protection (AP), wherein the ring amino group (—NH—) of a 3,7-dinitro-10H-phenothiazine is converted to a protected ring amino group (—$NR^{prot}$) for example:

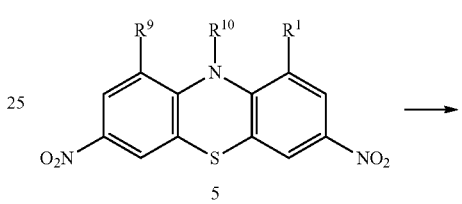

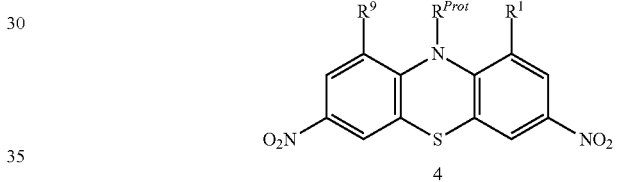

In one embodiment, ring amino protection is achieved as an acetate, for example, using acetic anhydride, for example, using acetic anhydride and pyridine.
In one embodiment, the nitro reduction (NR) step is:
(iii) nitro reduction (NR), wherein each of the nitro (—$NO_2$) groups of a protected 3,7-dinitro-10H-phenothiazine is converted to an amino (—$NH_2$) group, for example:

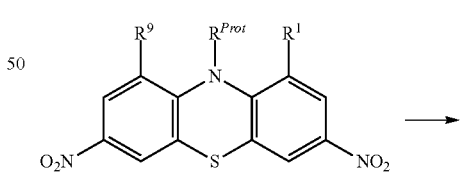

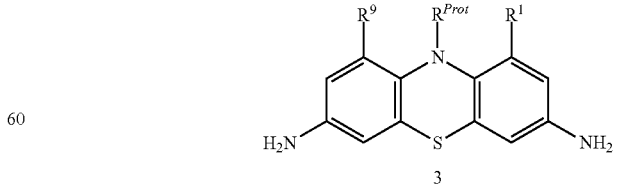

In one embodiment, nitro reduction may be performed using, for example, tin (II) chloride, for example, tin (II) chloride with ethanol.

In one embodiment, the amine substitution (AS) step is:

(iv) amine substitution (AS), wherein each of the amino (—NH$_2$) groups of a protected 3,7-diamino-10H-phenothiazine is converted to disubstituted amino group, for example:

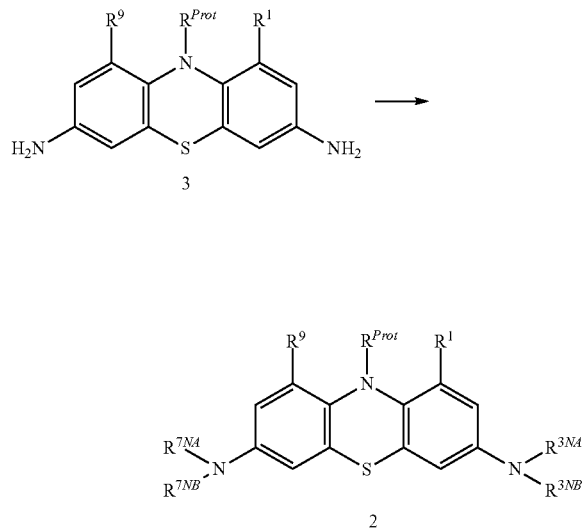

In one embodiment, amine substitution is performed using an alkyl halide, for example, an alkyl iodide, for example, methyl iodide, for example, methyl iodide with sodium hydroxide, DMSO, and tetra-n-butyl ammonium bromide.

In one embodiment, the ring amino deprotection (DP) step is:

(v) ring amino deprotection (DP), wherein the protecting group, R$^{Prot}$, is removed, for example:

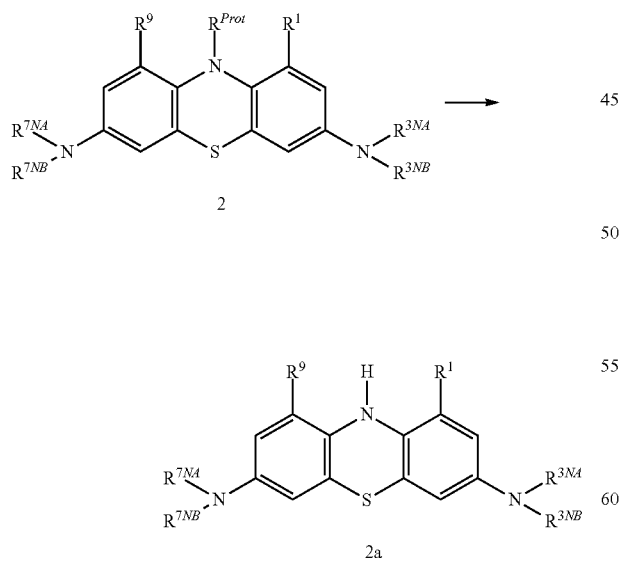

In one embodiment, ring amino deprotection may be performed using acid, for example, hydrochloric acid, for example, concentrated aqueous hydrochloric acid.

In one embodiment, the step is:

(vi) salt formation (SF), wherein the corresponding salt is formed, for example:

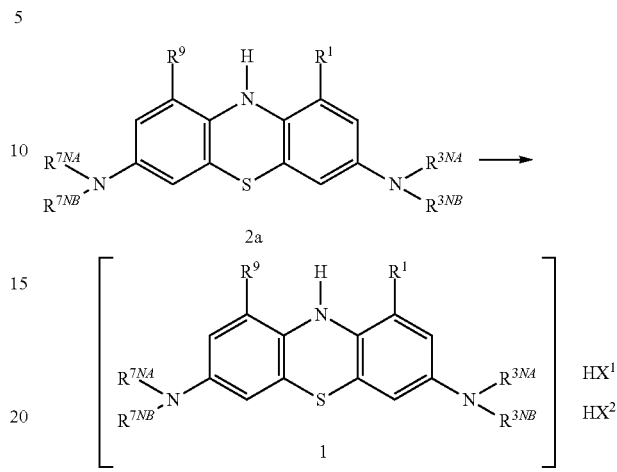

In one embodiment, salt formation may be performed using acid, for example, hydrochloric acid, for example, concentrated aqueous hydrochloric acid.

In one embodiment, the steps of ring amine deprotection and salt formation are performed simultaneously (i.e., as one step), for example, compound (1) is formed from compound (2) in one step.

In another approach, a suitable thioninium chloride (for example, methylthioninium chloride, MTC, also known as Methylene Blue) is converted to the corresponding halide, for example, by reaction with potassium iodide, for example, aqueous potassium iodide. The resulting thioninium iodide is then reduced, for example, with ethyl iodide and ethanol, and the corresponding salt formed. A similar method is described in Drew, H. D. K, and Head, F. S. H., "Derivatives of Methylene-blue," Journal of the Chemical Society, 1933, pp. 248-253. An example of such a method is illustrated in the following scheme.

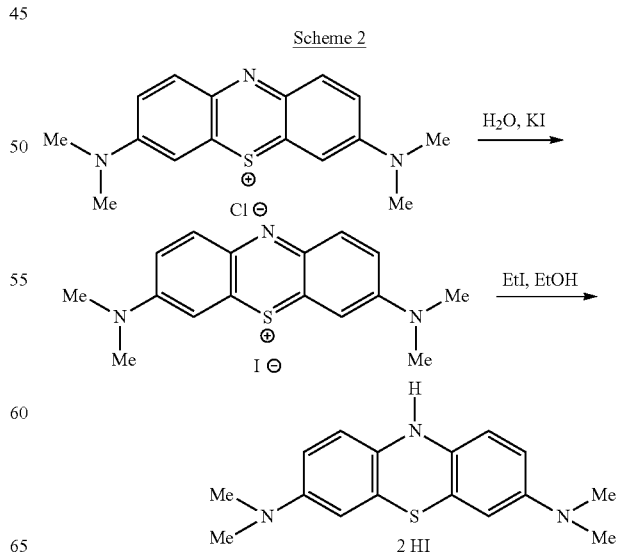

Thus, another aspect of the invention pertains to a method of preparing a 3,7-diamino-10H-phenothiazine (DAPTZ) compound of the following formula:

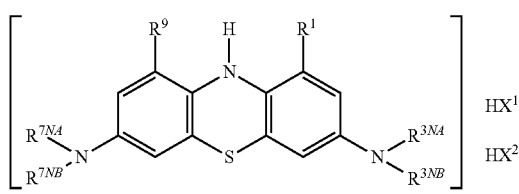

wherein $R^1$, $R^9$, $R^{3NA}$, $R^{3NB}$, $R^{7NA}$, $R^{7NB}$, $HX^1$ and $HX^2$ are as defined herein (for example, where $HX^1$ and $HX^2$ are each HI), comprising the step of:
(ii) reduction and iodide salt formation (RISF).

In one embodiment, the method comprises the steps of:
(i) iodide exchange (IE); and
(ii) reduction and iodide salt formation (RISF).

In one embodiment, the steps are performed in the order listed (i.e., any step in the list is performed at the same time as, or subsequent to, the preceding step in the list).

In one embodiment, the iodide exchange (IE) step is:
(i) iodide exchange (IE), wherein a 3,7-di(disubstituted amino)-thioninium salt is converted to the corresponding 3,7-di(disubstituted amino)-thioninium iodide, for example (where $Y^-$ is an anionic counter ion, for example, halide, for example, chloride or bromide):

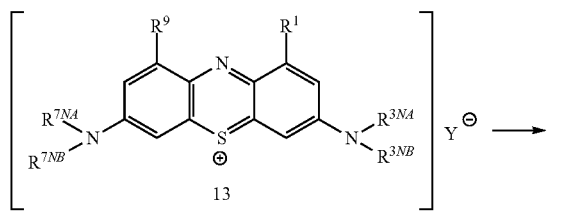

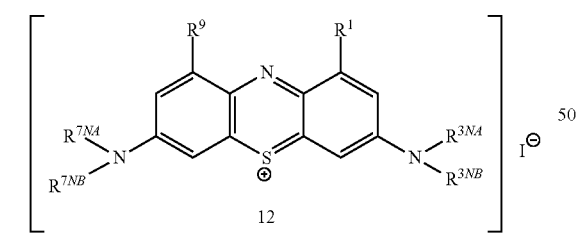

In one embodiment, iodide exchange (IE) is achieved by reaction with potassium iodide, for example, aqueous potassium iodide.

In one embodiment, the reduction and iodide salt formation (RISF) step is:
(ii) reduction and iodide salt formation (RISF), wherein a 3,7-di(disubstituted amino)-thioninium iodide is reduced and converted to the corresponding 3,7-diamino-10H-phenothiazine iodide compound, for example:

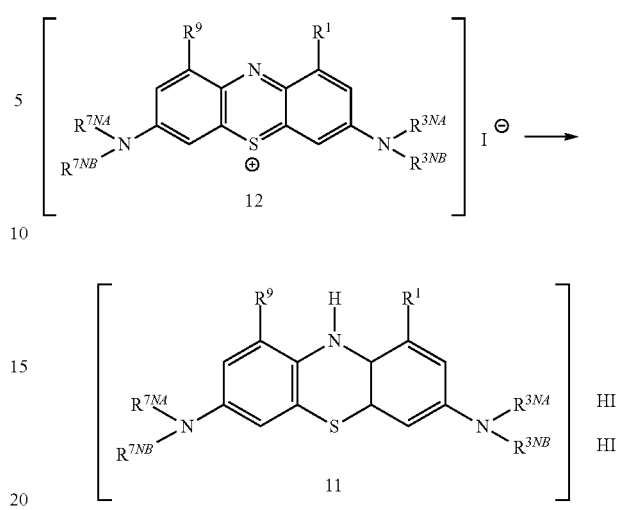

In one embodiment, reduction and iodide salt formation (RISF) is achieved by reaction with ethyl iodide, for example, ethyl iodide and ethanol.

In another approach, an appropriate thioninium salt, for example, ethyl thioninium semi zinc chloride, is simultaneously reduced and the ring amino group protected, for example, by reaction with phenylhydrazine, ethanol, acetic anhydride, and pyridine. The corresponding salt may then be prepared, for example, using concentrated aqueous hydrochloric acid, for example, at the same time as deprotection. An example of such a method is illustrated in the following scheme.

Scheme 3

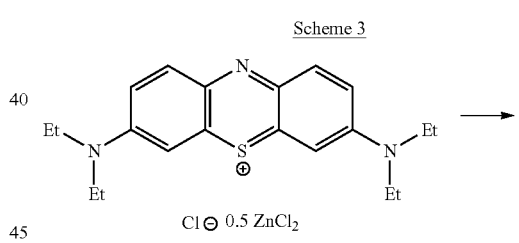

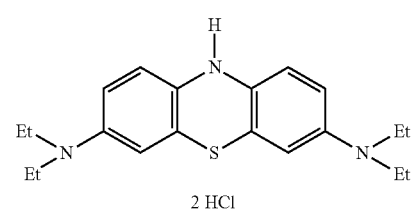

Thus, another aspect of the invention pertains to a method of preparing a 3,7-diamino-10H-phenothiazine (DAPTZ) compound of the following formula:

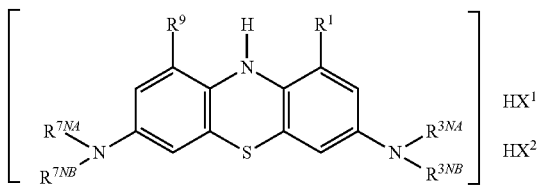

wherein $R^1$, $R^9$, $R^{3NA}$, $R^{3NB}$, $R^{7NA}$, $R^{7NB}$, $HX^1$ and $HX^2$ are as defined herein (for example,
where $HX^1$ and $HX^2$ are each HI), comprising the step of:
comprising the step of:
  (iv) salt formation (SF).
In one embodiment, the method comprises the steps of
  (iii) ring amino deprotection (DP), and
  (iv) salt formation (SF).
In one embodiment, the method comprises the steps of
  (ii) ring amino protection (AP),
  (iii) ring amino deprotection (DP), and
  (iv) salt formation (SF).
In one embodiment, the method comprises the steps of
  (i) reduction (RED)
  (ii) ring amino protection (AP),
  (iii) ring amino deprotection (DP), and
  (iv) salt formation (SF).
In one embodiment, the steps are performed in the order listed (i.e., any step in the list is performed at the same time as, or subsequent to, the preceding step in the list).

In one embodiment, the step of (i) reduction (RED) and the step of (ii) ring amino protection (AP) are performed simultaneously (i.e., as one step).

For example, in one embodiment, the combined reduction (RED) step and ring amino protection (AP) step is:
  (i) reduction (RED) and ring amino protection (AP), wherein a 3,7-di(disubstituted amino)-thioninium salt is reduced to give the corresponding 3,7-di(disubstituted amino)-10H-phenothiazine, and the ring amino group (—NH—) of the 3,7-di(disubstituted amino)-10H-phenothiazine is converted to a protected ring amino group (—$R^{Prot}$) to give the corresponding protected 3,7-di(disubstituted amino)-10H-phenothiazine, for example:

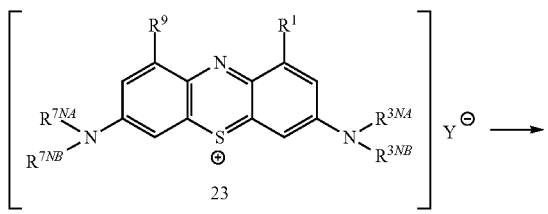

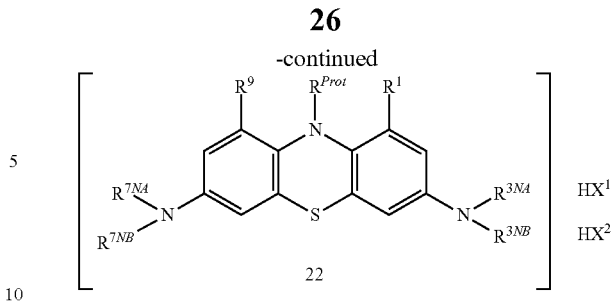

In one embodiment, Y represents cr.

In one embodiment, the combined reduction (RED) step and ring amino protection (AP) step is achieved using phenylhydrazine and acetic anhydride, for example, phenylhydrazine, ethanol, acetic anhydride, and pyridine.

In one embodiment, the step of (iii) ring amino deprotection (DP) and the step of (iv) salt formation (SF) are performed simultaneously (i.e., as one step).

For example, in one embodiment, the combined ring amino deprotection (DP) step and salt formation (SF) step is:
  (ii) ring amino deprotection (DP) and salt formation (SF), wherein the protecting group of a protected 3,7-di(disubstituted amino)-10H-phenothiazine is removed to give a 3,7-di(disubstituted amino)-10H-phenothiazine, and the corresponding salt is formed, for example:

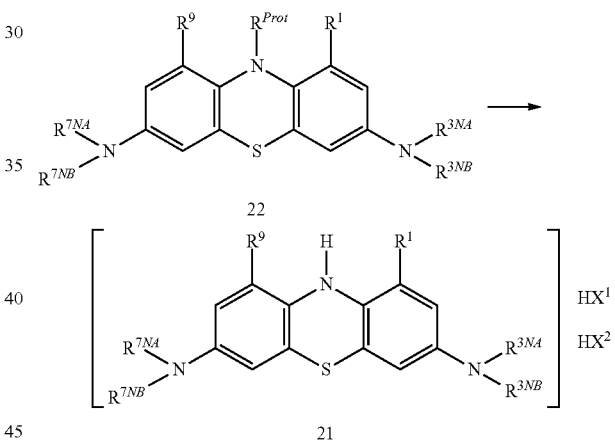

In one embodiment, the combined ring amino deprotection (DP) step and salt formation (SF) step may be performed using acid, for example, hydrochloric acid, for example, concentrated aqueous hydrochloric acid.

In a similar approach, an appropriate thioninium chloride (e.g., methyl thioninium chloride, ethyl thioninium chloride) is first reduced and acetylated to give the corresponding 1-(3,7-bis-dimethylamino-phenothiazin-10-yl)-ethanone,
  for example, by reaction with hydrazine ($NH_2NH_2$), methyl hydrazine ($MeNHNH_2$), or sodium borohydride ($NaBH_4$); and acetic anhydride (($H_3CCO)_2O$); for example, in the presence of a suitable base, for example, pyridine (C5H5N) or Hunig's base (diisopropylethylamine, $C_8H_{19}N$), for example, in a suitable solvent, for example, ethanol or acetonitrile. The reduced and acetylated compound is then deprotected (by removing the acetyl group), for example, by reaction with a suitable halic acid, for example, hydrochloric acid or hydrobromic acid, in a suitable solvent, for example, ethanol, and optionally with the addition of a suitable ether, for example, diethyl ether.

Compositions

Another aspect of the invention pertains to a composition comprising a DAPTZ compound, as described herein, and a pharmaceutically acceptable carrier or diluent.

Uses

Reversing and/or Inhibiting the Aggregation of a Protein

One aspect of the invention is the use of a DAPTZ compound, as described herein, to regulate (e.g., to reverse and/or inhibit) the aggregation of a protein, for example, aggregation of a protein associated with a neurodegenerative disease and/or clinical dementia. The aggregation may be in vitro, or in vivo, and may be associated with a disease state as discussed below.

Thus, one aspect of the invention pertains to a method of regulating (e.g., reversing and/or inhibiting) the aggregation of a protein, for example, aggregation of a protein associated with a neurodegenerative disease and/or clinical dementia, comprising contacting the protein with an effective amount of a DAPTZ compound, as described herein. The method may be performed in vitro, or in vivo.

Similarly, one aspect of the invention pertains to a method of regulating (e.g., reversing and/or inhibiting) the aggregation of a protein in the brain of a mammal, which aggregation is associated with a disease state as described herein, the treatment comprising the step of administering to said mammal in need of said treatment, a prophylactically or therapeutically effective amount of a DAPTZ compound, as described herein, that is an inhibitor of said aggregation.

Methods of Treatment

Another aspect of the present invention pertains to a method of treatment comprising administering to a patient in need of treatment a prophylactically or therapeutically effective amount of a DAPTZ compound, as described herein, preferably in the form of a pharmaceutical composition.

Use in Methods of Therapy

Another aspect of the present invention pertains to a DAPTZ compound, as described herein, for use in a method of treatment (e.g., of a disease condition) of the human or animal body by therapy.

Use in the Manufacture of Medicaments

Another aspect of the present invention pertains to use of a DAPTZ compound, as described herein, in the manufacture of a medicament for use in treatment (e.g., of a disease condition).

In one embodiment, the medicament comprises the DAPTZ compound.

Disease Conditions Treated—Diseases of Protein Aggregation

The DAPTZ compounds of the present invention are useful in the treatment or prophylaxis of diseases of protein aggregation.

Thus, in one embodiment, the disease condition is a disease of protein aggregation, and, for example, the treatment is with an amount of a DAPTZ compound, as described herein, sufficient to inhibit the aggregation of the protein associated with said disease condition.

In general, the protein aggregation is that which arises from an induced conformational polymerisation interaction, i.e., one in which a conformational change of the protein, or in a fragment thereof, gives rise to templated binding and aggregation of further (precursor) protein molecules in a self-propagating manner. Once nucleation is initiated, an aggregation cascade may ensue which involves the induced conformational polymerisation of further protein molecules, leading to the formation of toxic product fragments in aggregates which are substantially resistant to further proteolysis. The protein aggregates thus formed are thought to be a proximal cause of disease states manifested as neurodegeneration, clinical dementia, and other pathological symptoms.

The following Table provides a listing of various disease-associated aggregating proteins and the corresponding diseases of protein aggregation.

| | | Diseases of protein aggregation | | |
|---|---|---|---|---|
| Protein | Disease | Aggregating domain and/or mutations | Fibril subunit size (kDa) | Reference |
| | | Neuro-degenerative disorders | | |
| Prion protein | Prion diseases (CJD, nvCJD, Fatal familial insomnia, Gerstmann-Straussler-Scheinker syndrome, Kuru) | Inherited and sporadic forms PrP-27-30; many mutations. | 27 | Prusiner (1998) |
| | | Fibrillogenic domains: 113-120, 178-191, 202-218. | | Gasset et al. (1992) |
| Tau protein | Alzheimer's disease, Down's syndrome, FTDP-17, CBD, post-encephalitic parkinsonism, Pick's disease, parkinsonism with dementia complex of Guam | Inherited and sporadic forms | 10-12 | Wischik et al. (1988) |

Diseases of protein aggregation

| Protein | Disease | Aggregating domain and/or mutations | Fibril subunit size (kDa) | Reference |
|---|---|---|---|---|
| | | Truncated tau (tubulin-binding domain) 297-391. Mutations in tau in FTDP-17. Many mutations in presenilin proteins. | | Hutton et al. (1998) Czech et al. (2000) |
| Amyloid β-protein | Alzheimer's disease, Down's syndrome | Inherited and sporadic forms Amyloid β-protein; 1-42(3). 11 mutations in APP in rare families. | 4 | Glenner & Wong, (1984) Goate et al. (1991) |
| Huntingtin | Huntington's disease | N-termini of protein with expanded glutamine repeats. | 40 | DiFiglia et al. (1997) |
| Ataxins (1, 2, 3, 7) | Spinocerebellar ataxias (SCA1, 2, 3, 7) | Proteins with expanded glutamine repeats. | | Paulson et al. (1999) |
| Atrophin | Dentarubropallidoluysian atrophy (DRPLA) | Proteins with expanded glutamine repeats. | | Paulson et al. (1999) |
| Androgen receptor | Spinal and bulbar muscular atrophy | Proteins with expanded glutamine repeats. | | Paulson et al. (1999) |
| Neuroserpin | Familial encephalopathy with neuronal inclusion bodies (FENIB) | Neuroserpin; S49P, S52R. | 57 | Davis et al. (1999) |
| α-Synuclein | Parkinson's disease, dementia with Lewy bodies, multiple system atrophy | Inherited and sporadic forms | 19 | Spillantini et al. (1998) |
| | | A53T, A30P in rare autosomal-dominant PD families. | | Polymeropoulos et al. (1997) |
| Cystatin C | Hereditary cerebral angiopathy (Icelandic) | Cystatin C less 10 residues; L68Q. | 12-13 | Abrahamson et al. (1992) |
| Superoxide dismutase 1 | Amyotrophic lateral sclerosis | SOD1 mutations. | | Shibata et al. (1996) |

Non-neuro-degenerative disorders

| Protein | Disease | Aggregating domain and/or mutations | Fibril subunit size (kDa) | Reference |
|---|---|---|---|---|
| Haemoglobin | Sickle cell anaemia | Haemoglobin beta chain (S). | | Carrell & Gooptu (1998) |
| | Inclusion body haemolysis | Many mutations. | | |
| Serpins | α1-Antitrypsin deficiency (emphysema, cirrhosis) | Mutations | | Lomas et al. (1992) |
| | Antithrombin deficiency (thromboembolic disease) | Mutatons | | Carrell & Gooptu (1998) |
| | C1-inhibitor deficiency (angioedema) | Mutations | | Carrell & Gooptu (1998) |
| Immunoglobulin light chain | Plasma cell dyscrasias (primary systemic AL amyloidosis) | light chain or fragments. | 0.5-25 | Westermark et al. (1985) |
| Serum amyloid A | Reactive, secondary systemic AA amyloidosis | 76-residue fragment (critical residues 2-12). | 4.5-7.5 | Westermark et al. (1985) |
| | Chronic inflammatory disease | | | |

-continued

Diseases of protein aggregation

| Protein | Disease | Aggregating domain and/or mutations | Fibril subunit size (kDa) | Reference |
|---|---|---|---|---|
| Transthyretin | Familial amyloid polyneuropathy (systemic; FAP I) | Tetramer dissociated to conformational monomer variant. Many mutations (some not associated with amyloid; several different types of disease). | 10-14 | Gustavsson et al. (1991) |
| | Senile cardiac amyloidosis | Normal transthyretin | 10-14 | Gustavsson et al. (1991) |
| Gelsolin | Familial amyloidosis - Finnish type (FAP IV) | D187Q leads to truncated 173-225/243 (critical residues 182-192). | 9.5 | Maury & Baumann (1990) |
| $\beta$2-Microglobulin | Haemodialysis amyloidosis Prostatic amyloid | $\beta$2-Microglobulin | 12-25 | Gorevic et al. (1985) |
| Apolipoprotein AI | Familial amyloid polyneuropathy (systemic; FAP III) | N-terminal 83-93 residues; G26R, W50R, L60R | 9 | Booth et al. (1997) |
| Lysozyme | Familial visceral amyloidosis | Lysozyme or fragments (with or without I56T, D67H) | 14 | Pepys et al. (1993) |
| Amylin (Islet amyloid polypeptide) | Type II diabetes (NIDDM) | Fragments (critical core of 20-29); no mutations | 3.9 | Westermark (1990) |
| Fibrinogen $\alpha$-chain | Hereditary renal amyloidosis | Fibrinogen fragments | 7-10 | Uemichi et al. (1992) |
| Procalcitonin | Medullary carcinoma of thyroid | Calcitonin fragments | 3.4 | Sletten et al. (1976) |
| Atrial natriuretic factor | Cardiac amyloidosis | ANF, no mutants | 3.5 | Johansson et al. (1987) |
| Insulin | Injection localised amyloidosis | Insulin | | Dische et al. (1988) |
| Other proteins forming amyloid | (in vitro) | Other proteins | | Chiti et al. (1999) |

REFERENCES FOR THE ABOVE TABLE

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. *Nature* 385, 787-793.

Carrell, R. W. & Gooptu, B. (1998) Conformational changes and disease—serpins, prions and Alzheimer's. *Current Opinion in Structural Biology* 8, 799-809.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Rogues, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustaysson, A., Engström, U. & Westermark, P. (1991) Normal transthyretin and synthetic transthyretin fragments form amyloid-like fibrils in vitro. *Biochemical and Biophysical Research Communications* 175, 1159-1164.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Johansson, B., Wernstedt, C. & Westermark, P. (1987) Atrial natriuretic peptide deposited as atrial amyloid fibrils. *Biochemical and Biophysical Research Communications* 148, 1087-1092.

Lomas, D. A., Evans, D. L., Finch, J. T. & Carrell, R. W. (1992) The mechanism of Z a1-antitrypsin accumulation in the liver. *Nature* 357, 605-607.

Maury, C. P. & Baumann, M. (1990) Isolation and characterization of cardiac amyloid in familial amyloid polyneuropathy type IV (Finnish): relation of the amyloid protein to variant gelsolin. *Biochimica et Biophysica Acta* 1096, 84-86.

Paulson, H. L. (1999) Human genetics '99: trinucleotide repeats. *American Journal of Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Uemichi, T., Liuepnicks, J. j. & Benson, M. D. (1994) Hereditary renal amyloidosis with a novel variant fibrinogen. *Journal of Clinical Investigation* 93, 731-736.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H., O'Brien, T. D. & Betsholtz, C. (1992) Islet amyloid polypeptide—a novel controversy in diabetes research. *Diabetologia* 35, 297-303.

Westermark, P., Johnson, K. H. & Pitkanen, P. (1985) Systemic amyloidosis: A review with emphasis on pathogenesis. *Applied Physiology* 3, 55-68.

Wischik, C. M., Novak, M., Thøgersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

As described in WO 02/055720 and U.S. patent application No. 60/786,700 filed on 29 Mar. 2006 (title: Inhibitors of Protein Aggregation), diaminophenothiazines have utility in the inhibition of such protein aggregating diseases.

Thus it will be appreciated that, except where context requires otherwise, description of embodiments with respect to tau protein or tau-like proteins (e.g., MAP2), should be taken as applying equally to the other proteins discussed herein (e.g., 3-amyloid, synuclein, prion, etc.) or other proteins which may initiate or undergo a similar pathological aggregation by virtue of conformational change in a domain critical for propagation of the aggregation, or which imparts proteolytic stability to the aggregate this formed (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation, synuclein aggregation, etc. The same applies for "tau proteolytic degradation" etc.

Preferred Aggregating Disease Proteins

Preferred embodiments of the invention are based on tau protein. The term "tau protein," as used herein, refers generally to any protein of the tau protein family. Tau proteins are characterised as being one among a larger number of protein families which co-purify with microtubules during repeated cycles of assembly and disassembly (see, e.g., Shelanski et al., 1973, Proc. Natl. Acad. Sci. USA, Vol. 70, pp. 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (see, e.g., Matus, A., in "Microtubules" [Hyams and Lloyd, Eds.] pp. 155-166, John Wiley and Sons, New York, USA). MAP2 isoforms are almost identical to tau protein in the tandem repeat region, but differ substantially both in the sequence and extent of the N-terminal domain (see, e.g., Kindler and Garner, 1994, Mol. Brain Res., Vol. 26, pp. 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation, and so on.

In one embodiment, the protein is tau protein.

In one embodiment, the protein is a synuclein, e.g., α- or β-synuclein.

Where the protein is tau protein, in one embodiment of the present invention, there is provided a method of inhibiting production of protein aggregates (e.g. in the form of paired helical filaments (PHFs), optionally in neurofibrillary tangles (NFTs) in the brain of a mammal, the treatment being as described above.

Preferred Diseases of Protein Aggregation

Notably it is not only Alzheimer's disease (AD) in which tau protein (and aberrant function or processing thereof) may play a role. The pathogenesis of neurodegenerative disorders such as Pick's disease and Progressive Supranuclear Palsy (PSP) appears to correlate with an accumulation of pathological truncated tau aggregates in the dentate gyms and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford; especially Table 5.1). All of these diseases, which are characterized primarily or partially by abnormal tau aggregation, are referred to herein as "tauopathies".

Thus, in one embodiment, the disease condition is a tauopathy.

In one embodiment, the disease condition is a neurodegenerative tauopathy.

In one embodiment, the disease condition is Alzheimer's disease.

In one embodiment, treatment (e.g., treatment of a neurodegenerative tauopathy, e.g., Alzheimer's disease) may optionally be in combination with one or more other agents, for example, one or more cholinesterase inhibitors (such as Donepezil (also known as Aricept™), Rivastigmine (also known as Exelon™), Galantamine (also known as Reminyl™), NMDA receptor antagonists (such as Memantine (also known as Ebixa™ Namenda™), muscarinic receptor agonists, and/or inhibitors of amyloid precursor protein processing that leads to enhanced generation of beta-amyloid.

Disease Conditions Treated—Other Disease Conditions

In one embodiment, the disease condition is skin cancer.

In one embodiment, the disease condition is melanoma.

In one embodiment, the disease condition is a viral, bacterial or protozoal disease condition.

In one embodiment, the (protozoal) disease condition is malaria.

In this embodiment, treatment may be in combination with one or more antimicrobial agents, for example, chloroquine and/or atovaquone.

In one embodiment, the (viral) disease condition is caused by Hepatitis C, HIV, or West Nile Virus (WNV).

Other Uses

Another aspect of the present invention pertains to use of a DAPTZ compound, as described herein, in a method of inactivating a pathogen in a sample (for example a blood or plasma sample), comprising the steps of introducing the DAPTZ compound into the sample, and exposing the sample to light.

For example, in one embodiment, the method comprises the steps of introducing the DAPTZ compound into the sample, and then exposing the sample to light.

Use as Ligands

The DAPTZ compounds that are capable of inhibiting the aggregation of tau protein will also be capable of acting as ligands or labels of tau protein (or aggregated tau protein). Thus, in one embodiment, the DAPTZ compound is a ligand of tau protein (or aggregated tau protein).

Such DAPTZ compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic, or therapeutic application.

For example, in one embodiment, the DAPTZ compound is as defined herein, but with the additional limitation that the compound incorporates, is conjugated to, is chelated with, or is otherwise associated with, one or more (e.g., 1, 2, 3, 4, etc.) detectable labels, for example, isotopes, radioisotopes, positron-emitting atoms, magnetic resonance labels, dyes, fluorescent markers, antigenic groups, or therapeutic moieties.

In one embodiment, the DAPTZ compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in one embodiment, the DAPTZ compound is as defined above, but with the additional limitation that the compound incorporates, is conjugated to, is chelated with, or is otherwise associated with, one or more (e.g., 1, 2, 3, 4, etc.) detectable labels.

Labelled DAPTZ compounds (e.g., when ligated to tau protein or aggregated tau protein) may be visualised or detected by any suitable means, and the skilled person will appreciate that any suitable detection means as is known in the art may be used.

For example, the DAPTZ compound (ligand-label) may be suitably detected by incorporating a positron-emitting atom (e.g., $^{11}$C) (e.g., as a carbon atom of one or more alkyl group substituents, e.g., methyl group substituents) and detecting the compound using positron emission tomography (PET) as is known in the art.

Such $^{11}$C labelled DAPTZ compounds may be prepared by adapting the methods described herein in known ways, for example, in analogy to the methods described in WO 02/075318 (see FIGS. 11a, 11b, 12) and WO 2005/030676.

Thus, another aspect of the present invention pertains to a method of labelling tau protein (or aggregated tau protein) comprising the step of: (i) contacting the tau protein (or aggregated tau protein) with a DAPTZ compound that incorporates, is conjugated to, is chelated with, or is otherwise associated with, one or more (e.g., 1, 2, 3, 4, etc.) detectable labels.

Another aspect of the present invention pertains to a method of detecting tau protein (or aggregated tau protein) comprising the steps of: (i) contacting the tau protein (or aggregated tau protein) with a DAPTZ compound that incorporates, is conjugated to, is chelated with, or is otherwise associated with, one or more (e.g., 1, 2, 3, 4, etc.) detectable labels, and (ii) detecting the presence and/or amount of said compound bound to tau protein (or aggregated tau protein).

Another aspect of the present invention pertains to a method of diagnosis or prognosis of a tau proteinopathy in a subject believed to suffer from the disease, comprising the steps of: (i) introducing into the subject a DAPTZ compound capable of labelling tau protein or aggregated tau protein, particularly tau protein (e.g., a DAPTZ compound that incorporates, is conjugated to, is chelated with, or is otherwise associated with, one or more (e.g., 1, 2, 3, 4, etc.) detectable labels); (ii) determining the presence and/or amount of said compound bound to tau protein or aggregated tau protein in the brain of the subject; and (iii) correlating the result of the determination made in (ii) with the disease state of the subject.

Another aspect of the present invention pertains to a DAPTZ compound capable of labelling tau protein or aggregated tau protein (e.g., a DAPTZ compound that incorporates, is conjugated to, is chelated with, or is otherwise associated with, one or more (e.g., 1, 2, 3, 4, etc.) detectable labels), for use in a method of diagnosis or prognosis of a tau proteinopathy.

Another aspect of the present invention pertains to use of a DAPTZ compound capable of labelling tau protein or aggregated tau protein, particularly tau protein (e.g., a DAPTZ compound that incorporates, is conjugated to, is chelated with, or is otherwise associated with, one or more (e.g., 1, 2, 3, 4, etc.) detectable labels), in a method of manufacture of a diagnostic or prognostic reagent for use in the diagnosis or prognosis of a tau proteinopathy.

Those skilled in the art will appreciate that instead of administering DAPTZ ligands/labels directly, they could be administered in a precursor form, for conversion to the active form (e.g., ligating form, labelling form) by an activating agent present in, or administered to, the same subject.

The ligands disclosed herein may be used as part of a method of diagnosis or prognosis. It may be used to select a patient for treatment, or to assess the effectiveness of a treatment or a therapeutic (e.g., an inhibitor of tau protein aggregation) administered to the subject.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of a DAPTZ compound, or a material, composition or dosage from comprising a DAPTZ compound, which is effective for producing some desired therapeutic effect, commensurate with a reasonable benefit/risk ratio, when administered in accordance with a desired treatment regimen.

Similarly, the term "prophylactically effective amount," as used herein, pertains to that amount of a DAPTZ compound, or a material, composition or dosage from comprising a DAPTZ compound, which is effective for producing some desired prophylactic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

For example, it may be beneficial to combine treatment with a DAPTZ compound as described herein with one or more other (e.g., 1, 2, 3, 4) agents or therapies.

The particular combination would be at the discretion of the physician who would select dosages using his/her common general knowledge and dosing regimens known to a skilled practitioner.

The agents (i.e., a DAPTZ compound as described here, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., a DAPTZ compound as described here, plus one or more other agents) may be formulated together in a single dosage form, or alternatively, the individual agents may be formulated separately and presented together in the form of a kit, optionally with instructions for their use.

Routes of Administration

The DAPTZ compound, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

In one embodiment, the subject/patient is not a human.

Formulations

While it is possible for the DAPTZ compound to be used (e.g., administered) alone, it is often preferable to present it as a composition or formulation.

In one embodiment, the composition is a pharmaceutical composition (e.g., formulation, preparation, medicament) comprising a DAPTZ compound, as described herein, and a pharmaceutically acceptable carrier, diluent, or excipient.

In one embodiment, the composition is a pharmaceutical composition comprising at least one DAPTZ compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled DAPTZ compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the DAPTZ compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the DAPTZ compound with a carrier which constitutes one or more accessory ingredients. In general, the formulations are prepared by uniformly and intimately bringing into association the DAPTZ compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the DAPTZ compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the DAPTZ compound in the liquid is from about 1 ng/ml to about 10 ng/ml, for example from about 10 ng/ml to about 1 ng/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

EXAMPLES OF SOME PREFERRED FORMULATIONS

One aspect of the present invention pertains to a dosage unit (e.g., a pharmaceutical tablet or capsule) comprising 20 to 300 mg of a DAPTZ compound as described herein (e.g., obtained by, or obtainable by, a method as described herein; having a purity as described herein; etc.), and a pharmaceutically acceptable carrier, diluent, or excipient.

In one embodiment, the dosage unit is a tablet.

In one embodiment, the dosage unit is a capsule.

In one embodiment, the amount is 30 to 200 mg.

In one embodiment, the amount is about 30 mg.

In one embodiment, the amount is about 60 mg.

In one embodiment, the amount is about 100 mg.

In one embodiment, the amount is about 150 mg.

In one embodiment, the amount is about 200 mg.

In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Dosage

It will be appreciated by one of skill in the art that appropriate dosages of the DAPTZ compound, and compositions comprising the DAPTZ compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the DAPTZ compound is in the range of about 100 ng to about 25 mg (more typically about 1 µg to about 10 mg) per kilogram body weight of the subject per day.

In one embodiment, the DAPTZ compound is administered to a human patient according to the following dosage regime: about 100 mg, 3 times daily.

In one embodiment, the DAPTZ compound is administered to a human patient according to the following dosage regime: about 150 mg, 2 times daily.

In one embodiment, the DAPTZ compound is administered to a human patient according to the following dosage regime: about 200 mg, 2 times daily.

EXAMPLES

The following examples are provided solely to illustrate the present invention and are not intended to limit the scope of the invention, as described herein.

Chemical Synthesis

Synthesis 1

3-Nitro-10H-phenothiazine

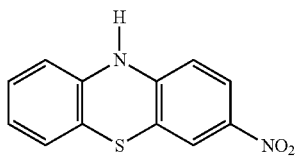

Sodium nitrite (20.00 g, 210 mmol) was added to a mixture of 10H-phenothiazine (20.00 g, 50 mmol), chloroform (100 cm$^3$), and acetic acid (20 cm$^3$), and the mixture was stirred for 1 hour at room temperature. Acetic acid (20 cm$^3$) was then added and the mixture was stirred for a further 18 hours. The suspension was filtered and washed with acetic acid, ethanol, water, and finally ethanol to give a purple/brown solid. The residue was dissolved in hot DMF and allowed to cool before filtering the di-nitro compound as a purple solid. Concentration of the DMF solution and washing the precipitate with water and methanol gave the title mono-nitro compound (15 g, ~50%) as a brown solid; $v_{max}$ (KBr)/cm$^{-1}$: 3328 (NH), 3278 (NH), 3229 (NH), 3119 (CH), 3049 (CH), 1557 (NO$_2$), 1531 (NO$_2$); $\delta_H$ (250 MHz; DMSO): 6.64 (5H, m, ArH), 7.68 (1H, d, J2.5, ArH), 7.79-7.84 (1H, dd, J2.75, 6.5, ArH); $\delta_C$ (62.9 MHz; DMSO): 113.3 (ArC), 115.3 (ArC), 116.9 (ArC), 121.8 (ArC), 123.6 (ArC), 123.7 (ArC), 124.6 (ArC), 126.4 (ArC), 128.1 (ArC), 138.8 (ArC), 141.0 (ArC), 147.8 (ArC).

Synthesis 2

3,11-Dinitro-10H-phenothiazine

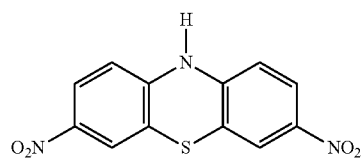 [SMILES: O=[N+]([O-])c1ccc2c(c1)Sc1cc([N+](=O)[O-])ccc1N2]

The procedure for the synthesis of 3-nitro-10H-phenothiazine was followed using 3-nitro-10H-phenothiazine (10.00 g, 41 mmol), chloroform (40 cm$^3$), acetic acid (2×10 cm$^3$), and sodium nitrite (11.86 g, 173 mmol). The residue obtained was recrystallised from DMF to yield the title di-nitro compound (6.60 g 56%) as purple needles; $v_{max}$ (KBr)/cm$^{-1}$: 3331 (NH), 3294 (NH), 3229 (NH), 3101 (CH), 3067 (CH), 1602 (NO$_2$), 1558 (NO$_2$); $\delta_H$ (250 MHz; DMSO): 6.73-6.76 (2H, d, J9, ArH), 7.78 (2H, s, ArH), 7.89-7.85 (2H, d, J9, ArH).

Synthesis 3

1-(3,7-Dinitro-phenothiazin-10-yl)-ethanone

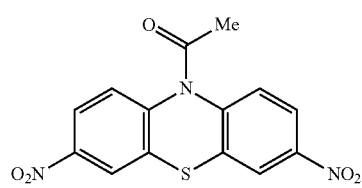

A solution of 3,11-dinitro-10H-phenothiazine (3.00 g, 10.37 mmol), acetic anhydride (15.88 g, 155.50 mmol), and pyridine (30 cm$^3$) was stirred at reflux for 18 hours. The warm solution was then carefully poured over ice water. A precipitate formed and was filtered, dissolved in dichloromethane, dried over magnesium sulphate, filtered, and concentrated to give a brown/orange solid, which was purified by column chromatography (SiO$_2$, ethyl acetate:petroleum ether, 2:3, loaded as a dichloromethane solution) to give the title compound (2.46 g, 71%) as a light yellow solid which can be recrystallised from acetone to give light yellow needles; $v_{max}$ (KBr)/cm$^{-1}$: 3091 (CH), 3063 (CH), 1680 (C=O), 1575 (NO$_2$), 1510 (NO$_2$); $\delta_H$(250 MHz; CDCl$_3$): 2.28 (3H, s, CH$_3$), 7.65-7.69 (2H, d, J9, ArH), 8.22-8.26 (2H, dd, J2.75, 8.75, ArH), 8.33-8.32 (2H, d, J2.5, ArH); $\delta_C$(62.9 MHz; CDCl$_3$): 168.2 (C=O), 146.3 (ArC), 143.3 (ArC), 133.6 (ArC), 127.8 (ArC), 123.4 (ArC), 122.9 (ArC), 23.1 (CH$_3$); m/z (ES) 331.0 (80%, [M]$^+$).

Synthesis 4

1-(3,7-Diamino-phenothiazin-10-yl)-ethanone

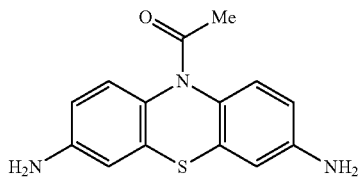 [SMILES: CC(=O)N1c2ccc([N+](=O)[O-])cc2Sc2cc([N+](=O)[O-])ccc21]

A mixture of 1-(3,7-dinitro-phenothiazin-10-yl)-ethanone (2 g, 6.04 mmol), tin (II) chloride dihydrate (14.17 g, 62.8 mmol), and ethanol (50 cm$^3$) was heated to reflux and stirred at this temperature for 5 hours. The mixture was then cooled to room temperature and poured over ice water. The pH was adjusted to 7 with 5% sodium hydrogen carbonate before the product was extracted with ethyl acetate (3×50 cm$^3$). The extracts were washed with brine and dried over magnesium sulphate, filtered, and concentrated to give the title compound (1.64 g, 100%) as a purple blue solid; $v_{max}$ (KBr)/cm$^{-1}$: 3445 (NH), 3424 (NH), 3368 (NH), 3322 (NH), 3203 (NH), 3054 (CH), 2995 (CH), 1706 (C=O), 1650 (NO$_2$), 1590 (NO$_2$); $\delta_H$ (250 MHz; CDCl$_3$): 2.01 (3H, s, CH$_3$), 5.09-5.43 (4H, brd s, NH), 6.47-6.51 (2H, dd, J1.5, 8.25, ArH), 6.61 (2H, s, ArH), 7.11-7.15 (2H, d, J8, ArH); $\delta_C$ (62.9 MHz; CDCl$_3$): 169.1 (C=O), 147.2 (ArC), 128.1 (ArC), 127.6 (ArC), 127.3 (ArC), 112.3 (ArC), 111.5 (ArC), 22.6 (CH$_3$); m/z (ES) 293.9 (95%, [M+H, Na])$^+$), 272.0 (20%, [M+H]$^+$), 227.9 (100%, [M+H, —Ac]$^+$).

Synthesis 5

3,7-Diamino-phenothiazine bis(hydrogen chloride) (B4)

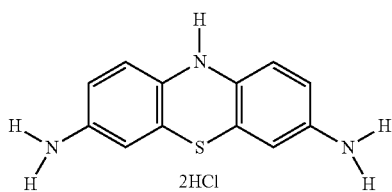 [SMILES: Nc1ccc2c(c1)Sc1cc(N)ccc1N2]

1-(3,7-Diamino-phenothiazin-10-yl)-ethanone (0.25 g, 0.921 mmol) was dissolved in aqueous hydrochloric acid (5N, 10 cm$^3$) and the solution was heated to reflux and stirred for 30 minutes. Concentration of the reaction mixture gave the title compound as a light blue solid. $\delta_H$ (250 MHz; D$_2$O): 6.60 (2H, brd d, ArH), 7.07 (4H, brd s, ArH).

Synthesis 6

1-(3,7-Bis-dimethylamino-phenothiazin-10-yl)-ethanone

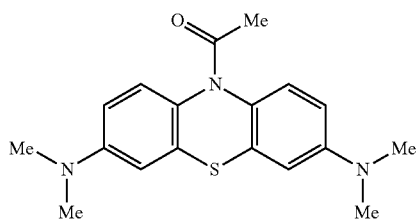 [SMILES: CC(=O)N1c2ccc(N(C)C)cc2Sc2cc(N(C)C)ccc21]

1-(3,7-Diamino-phenothiazin-10-yl)-ethanone (0.25 g 0.92 mmol) was dissolved in DMSO (3 cm$^3$). Toluene (10 cm$^3$), iodomethane (1.96 g, 13.8 mmol), tetrabutylammonium bromide (50 mg), and finally aqueous sodium hydroxide solution (50%, 1.25 cm$^3$) were added. The mixture was stirred at room temperature for 2 hours. Additional aqueous sodium hydroxide (50%, 1.25 cm$^3$) and iodomethane (1.96 g, 13.8 mmol) were then added. The mixture was allowed to stir for a further 3 hours at room temperature before a third aliquot of aqueous sodium hydroxide (50%, 1.25 cm$^3$) and iodomethane (1.96 g, 13.8 mmol) were added and the mixture stirred for a further 18 hours. The thick suspension was washed with water (3×75 cm$^3$) and the toluene extract collected. The water was extracted with dichloromethane (3×50 cm$^3$) and the extracts combined with the toluene, and dried over magnesium sulphate, filtered, and concentrated to give a deep purple solid. The residue was purified by column chromatography (SiO$_2$, ethyl acetate:petroleum ether, 2:3, loaded as a dichloromethane solution) to give the title compound product (0.12 g, 40%) as a light purple solid; $v_{max}$ (KBr)/cm$^{-1}$: 2910 (CH), 2876 (CH), 2856 (CH), 2799 (CH), 1659 (C=O), 1596 (NO$_2$), 1502 (NO$_2$); $\delta_H$ (250 MHz; CDCl$_3$): 2.16 (3H, s, CH$_3$), 2.93 (12H, s, NCH$_3$), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl$_3$): 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$).

Synthesis 7

N,N,N',N'-Tetramethyl-10H-phenothiazine-3,7-diamine bis(hydrogen chloride) (B3)

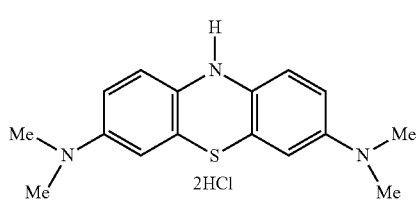 [SMILES: CN(C)c1ccc2c(c1)Sc1cc(N(C)C)ccc1N2]

1-(3,7-Bis-dimethylamino-phenothiazin-10-yl)-ethanone (0.5 g, 1.84 mmol) was dissolved in aqueous hydrochloric acid (5N, 15 cm$^3$), and the solution was heated to reflux temperature and stirred for 30 minutes. Concentration of the reaction mixture gave the title compound as a green/blue solid; $\delta_H$ (250 MHz; D$_2$O): 3.18 (12H, s, NCH$_3$), 6.67 (2H, d, J8.5, ArH), 7.16 (4H, brd s, ArH); $\delta_C$ (62.9 MHz; D$_2$O):

144.3 (ArC), 138.9 (ArC), 122.4 (ArC), 120.8 (ArC), 120.7 (ArC), 117.6 (ArC), 48.9 (NCH$_3$).

Synthesis 8

Methylthioninium Iodide

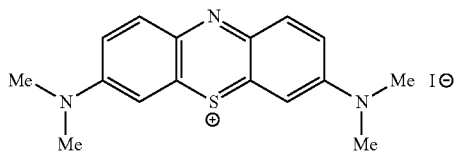 [SMILES: CN(C)c1ccc2nc3ccc(N(C)C)cc3[s+]c2c1 ; [I-]]

To a round bottom flask was added methylthioninium chloride (MTC, Methylene Blue) (2 g, 6.25 mmol) and water (50 cm$^3$) and the mixture stirred for 10 minutes or until the solid dissolved. Potassium iodide (1.56 g, 9.4 mmol) was then added to the mixture and a green black suspension formed. The reaction was heated to boiling and allowed to cool naturally giving the title compound (2.03 g, 79%) as bright green needles. Anal. Calcd for C$_{16}$H$_{18}$N$_3$SI:C, 46.72; H, 4.41; N, 10.22; S, 7.80; I, 30.85. Found: C, 46.30; H, 4.21; N, 10.14; S, 7.86; I, 29.34.

Synthesis 9

N,N,N',N'-Tetramethyl-10H-phenothiazine-3,7-diamine bis(hydrogen iodide) (B6)

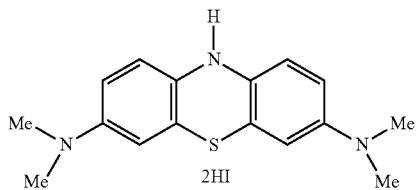 [SMILES: CN(C)c1ccc2c(c1)Sc1cc(N(C)C)ccc1N2]

To a round bottom flask was added methylthioninium iodide (2 g, 4.86 mmol), ethanol (100 cm$^3$) and ethyl iodide (75.8 g, 486 mmol) and the mixture was heated at reflux for 18 hours where the colour changed from green/blue to brown with a yellow precipitate. Once cooled to room temperature, the mixture was filtered and washed with diethylether (20 cm$^3$) to give the title compound (1.99 g, 76%) as a light green solid. δ$_H$ (250 MHz; D$_2$O): 3.20 (12H, s, NCH$_3$), 6.76 (2H, d, J8.5, ArH), 7.22 (2H, brd s, ArH); δ$_C$ (62.9 MHz; D$_2$O): 145.0 (ArC), 139.3 (ArC), 122.6 (ArC), 121.1 (ArC), 120.9 (ArC), 117.9 (ArC), 48.9 (NCH$_3$).

Synthesis 10

1-(3,7-Bis-diethylamino-phenothiazin-10-yl)-ethanone

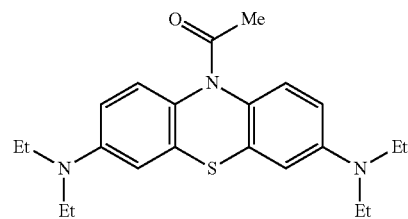 [SMILES: CCN(CC)c1ccc2c(c1)Sc1cc(N(CC)CC)ccc1N2C(C)=O]

To a dry 25 cm$^3$ round bottom flask was added ethylthioninium zinc chloride (0.5 g, 1.13 mmol) and ethanol (10 cm$^3$). Phenylhydrazine (0.134 g, 1.24 mmol) was then added dropwise under an atmosphere of nitrogen. The mixture was stirred 25° C. for 1 hour and concentrated under high vacuum. Pyridine (50 cm$^3$) and acetic anhydride was added and the mixture stirred for 18 hours at 60° C. The solution was opened to ice/water (250 cm$^3$) and the organics were extracted into ethyl acetate (3×50 cm$^3$). The extracts were washed with saturated copper sulphate solution and dried over magnesium sulphate, filtered, and concentrated to give the crude product as a brown oil, which was purified using flash column chromatography with an eluent of 40% ethylacetate: 60% petroleum spirit 40-60° C. and silica 40-63µ 60 Å to give the title compound (0.18 g, 41%) as a green glassy solid. δ$_H$ (250 MHz; CDCl$_3$): 7.0-7.5 (2H, brds, ArH), 6.64 (2H, s, ArH), 6.52 (2H, d, ArH), 3.35 (8H, q, 7, NCH$_2$), 2.18 (3H, s, CH$_3$), 1.16 (12H, t, 7, CH$_3$); δ$_C$ (62.9 MHz; CDCl$_3$): 12.5 (CH$_3$), 22.9 (CH$_3$), 44.6 (NCH$_2$), 110.1 (ArC), 127.4 (ArC), 146.5 (ArC), 170.2 (C=O).

Synthesis 11

N,N,N',N'-Tetraethyl-10H-phenothiazine-3,7-diamine bis(hydrogen chloride)

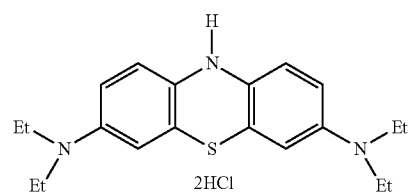 [SMILES: CCN(CC)c1ccc2c(c1)Sc1cc(N(CC)CC)ccc1N2]

To a 25 cm$^3$ round bottom flask was added 3,7-diethylamino-10-acetyl-phenothiazine (0.125 g, 0.33 mmol) and aqueous hydrochloric acid (5 M, 5 cm$^3$). The mixture was heated at 100° C. for 2 hours before cooling to room temperature and was concentrated to give the title compound (0.11 g, 81%) as a yellow green glassy solid. δ$_H$ (250 MHz; CD$_3$OD): 7.07 (4H, brd, ArH), 6.65 (2H, brd, ArH), 3.35 (8H, brd, NCH$_2$), 0.97 (12H, brd, CH$_3$); δ$_C$ (62.9 MHz; CD$_3$OD): 10.8 (CH$_3$), 55.1 (NCH$_2$), 116.6 (ArC), 120.4 (ArC), 121.5 (ArC), 123.6 (ArC), 132.6 (ArC), 144.5 (ArC).

Synthesis 12

1-(3,7-Bis-dimethylamino-phenothiazin-10-yl)-ethanone

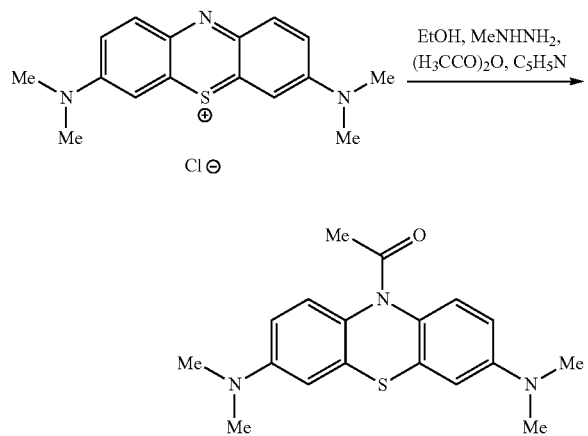 [SMILES: CN(C)c1ccc2nc3ccc(N(C)C)cc3[s+]c2c1 ; [Cl-] ; CC(=O)N1c2ccc(N(C)C)cc2Sc2cc(N(C)C)ccc21]

Synthesis using methylhydrazine/pyridine in two pots. To a 250 cm³ round bottom flask placed under an atmosphere of argon was added methylthioninium chloride trihydrate (26.74 mmol, 10 g), ethanol (100 cm³) and methylhydrazine (58.83 mmol, 2.71 g). The mixture was heated to 40° C. and stirred for 2 hours. The yellow/green suspension was cooled to 5° C. and filtered under argon, washed with ethanol (20 cm³) and dried to give leuco-methylene blue as a light green solid. To the leuco product was added acetic anhydride (40 cm³) and pyridine (10 cm³) and the solution was heated at 100° C. for 18 hours. The cooled mixture was then poured carefully over ice water while stirring to give a precipitate, which was filtered, washed with water, and dried at 60° C. for 2 hours to yield the title compound (5.82 g, 66%) as a light brown solid. Mp 137° C.; $v_{max}$(KBr)/cm⁻¹ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J8.5, ArH), 6.69-6.71 (2H, d, J 2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 13

1-(3,7-Bis-dimethylamino-phenothiazin-10-yl)-ethanone

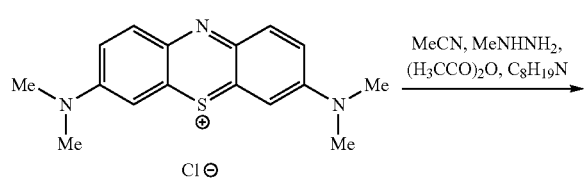

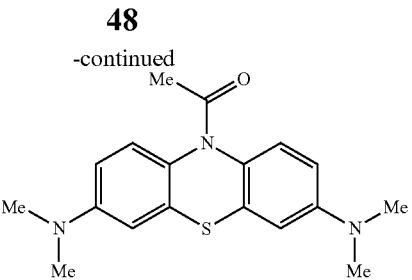

Synthesis using methylhydrazine/Hunig's base in one pot. To a 5000 cm³ reactor vessel under an atmosphere of nitrogen was added methylthioninium chloride trihydrate (0.54 mol, 200 g) and acetonitrile (1000 cm³). Methylhydrazine (1.07 mol, 49.36 g) was added dropwise at 1.5 mL per minute. The temperature of the mixture increased to 32° C. and was stirred for 20 minutes. The yellow/green suspension had acetic anhydride (5.35 mol, 541 g) added and then Hunig's base (diisopropylethylamine) (1.55 mol, 200 g) was added. The mixture was heated at 90° C. for 2 hours. The cooled mixture was then poured carefully into ice water (2000 cm³) in ten 200 cm³ portions while stirring to give a precipitate. The precipitate was stirred for 45 minutes before it was filtered, washed with water (3×250 cm³). and air dried for 30 minutes. The crude material was crystallised from hot ethanol (2750 cm³) to yield the title compound (112.1 g, 64%) as a light grey solid. Mp 137° C.; $v_{max}$(KBr)/cm⁻¹ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 14

1-(3,7-Bis-dimethylamino-phenothiazin-10-yl)-ethanone

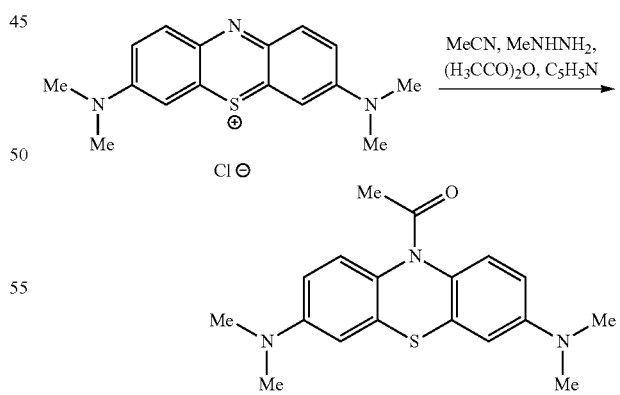

Synthesis using methylhydrazine/pyridine in one pot. To a 250 cm³ round bottom flask under an atmosphere of nitrogen was added methylthioninium chloride trihydrate (26.74 mmol, 10 g) and acetonitrile (50 cm³). Methylhydrazine (53.5 mmol, 2.46 g) was added in four equal portions over a 30 minutes time period. The temperature of the mixture was maintained at 35° C. with a cold water bath and was stirred for 30 minutes. The yellow/green suspension had acetic anhydride (267 mmol, 27.3 g) and pyridine (80.2 mmol, 6.35 g) was added. The mixture was heated at 90° C. for 2 hours. The cooled mixture was then poured carefully into ice water (200 cm$^3$) in ten equal portions while stirring to give a precipitate. The precipitate was stirred for 30 minutes before it was filtered, washed with water (3×50 cm$^3$) and air dried for 30 minutes. The crude material was crystallised from hot ethanol (120 cm$^3$) to yield the title compound (5.97 g, 68%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M–OAc]$^+$), 328.1 (15%, [M+H]$^+$), 350.1 (41%, [M+Na]$^+$).

Synthesis 15

1-(3,7-Bis-dimethylamino-phenothiazin-10-yl)-ethanone

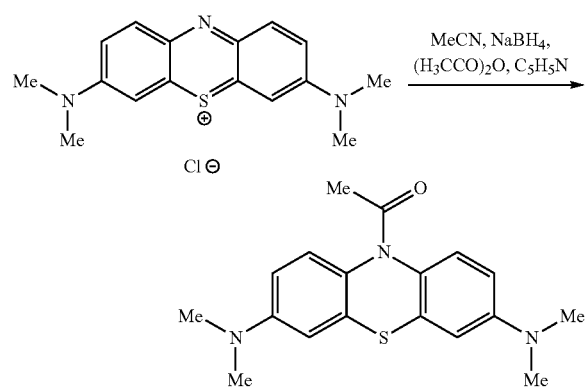

Synthesis using sodium borohydride/pyridine in one pot. To a 500 cm$^3$ round bottom flask under an atmosphere of nitrogen was added methylthioninium chloride trihydrate (0.134 mol, 50 g) and acetonitrile (250 cm$^3$). Sodium borohydride (0.174 mol, 6.6 g) was added in four equal portions over a 30 minute time period. The temperature of the mixture was maintained at 35° C. with a cold water bath and was stirred for 30 minutes. The yellow/green suspension had acetic anhydride (0.535 mol, 55 g) and pyridine (0.174 mol, 13.76 g) added. The mixture was heated at 90° C. for 2 hours. The cooled mixture was then poured carefully into ice water (250 cm$^3$) in ten equal portions while stirring to give a precipitate. The precipitate was stirred for 30 minutes before it was filtered, washed with water (3×50 cm$^3$), and air dried for 30 minutes. The crude material was crystallised from hot ethanol (500 cm$^3$) to yield the title compound (26.7 g, 61%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M–OAc]$^+$), 328.1 (15%, [M+H]$^+$), 350.1 (41%, [M+Na]$^+$).

Synthesis 16

1-(3,7-Bis-dimethylamino-phenothiazin-10-yl)-ethanone

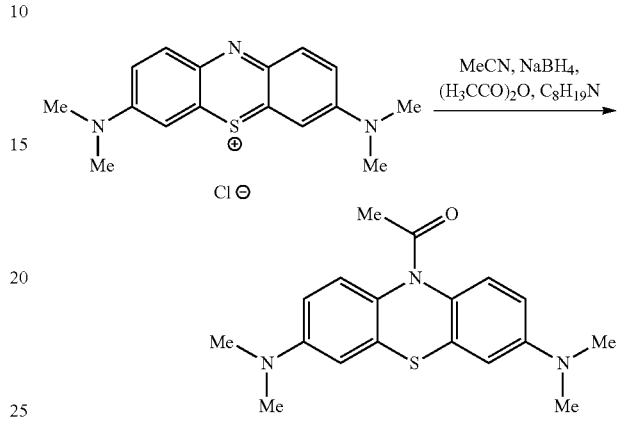

Synthesis using sodium borohydride/Hunig's base in one pot. To a 500 cm$^3$ round bottom flask under an atmosphere of nitrogen was added methylthioninium chloride trihydrate (80.2 mmol, 30 g) and acetonitrile (150 cm$^3$). Sodium borohydride (104 mmol, 3.94 g) was added in four equal portions over a 30 minute time period. The temperature of the mixture was maintained at 35° C. with a cold water bath and was stirred for 30 minutes. The yellow/green suspension had acetic anhydride (321 mmol, 32.75 g) and Hunig's base (diisopropylethylamine) (120 mmol, 15.55 g) added. The mixture was heated at 90° C. for 2 hours. The cooled mixture was then poured carefully into ice water (200 cm$^3$) in ten equal portions while stirring to give a precipitate. The precipitate was stirred for 30 minutes before it was filtered, washed with water (3×50 cm$^3$), and air dried for 30 minutes. The crude material was crystallised from hot ethanol (300 cm$^3$) to yield the title compound (13.55 g, 52%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M–OAc]$^+$), 328.1 (15%, [M+H]$^+$), 350.1 (41%, [M+Na]$^+$).

Synthesis 17

1-(3,7-Bis-dimethylamino-phenothiazin-10-yl)-ethanone

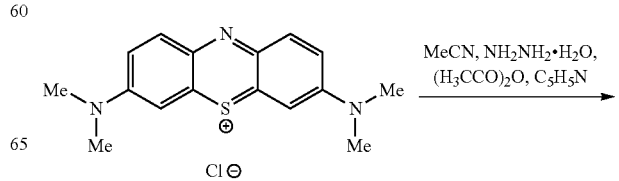

-continued

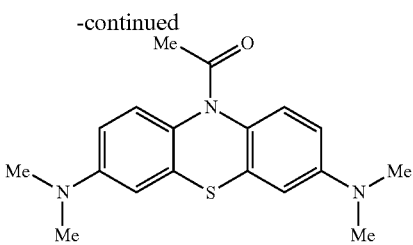

Synthesis using hydrazine monohydrate/pyridine in one pot. To a 250 cm³ round bottom flask under an atmosphere of nitrogen was added methylthioninium chloride trihydrate (26.74 mmol, 10 g) and acetonitrile (50 cm³). Hydrazine monohydrate (58.8 mmol, 2.95 g) was added and the mixture was heated to reflux and stirred for 10 minutes before cooling to 25° C. The yellow/green suspension had acetic anhydride (424 mmol, 43.3 g) and pyridine (124 mmol, 9.78 g) added. The mixture was heated at 90° C. for 2 hours. The cooled mixture was then poured carefully into ice water (100 cm³) in ten equal portions while stirring to give a precipitate. The precipitate was stirred for 30 minutes before it was filtered, washed with water (3×50 cm³), and air dried for 30 minutes. The crude material was crystallised from hot ethanol (100 cm³) to yield the title compound (4.87 g, 56%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 18

1-(3,7-Bis-dimethylamino-phenothiazin-10-yl)-ethanone

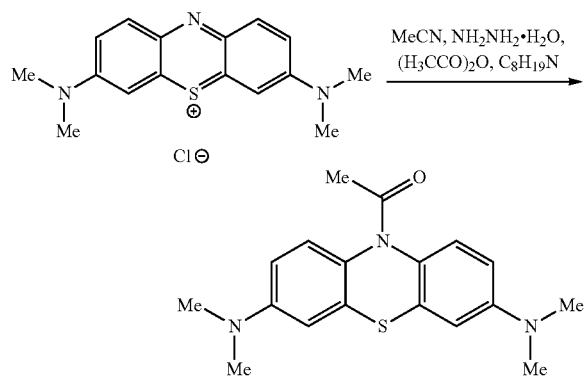

Synthesis using hydrazine monohydrate/Hunig's base in one pot. To a 250 cm³ round bottom flask under an atmosphere of nitrogen was added methylthioninium chloride trihydrate (80.2 mmol, 30 g) and acetonitrile (150 cm³). Hydrazine monohydrate (176.5 mmol, 8.84 g) was added and the mixture was heated to reflux and stirred for 10 minutes before cooling to 25° C. The yellow/green suspension had acetic anhydride (794 mmol, 81.2 g) and Hunig's base (diisopropylethylamine) (232 mmol, 29.97 g) added. The mixture was heated at 90° C. for 2 hours. The cooled mixture was then poured carefully into ice water (400 cm³) in ten equal portions while stirring to give a precipitate. The precipitate was stirred for 30 minutes before it was filtered, washed with water (3×100 cm³), and air dried for 30 minutes. The crude material was crystallised from hot ethanol (400 cm³) to yield the title compound (17.15 g, 65%) as a light grey solid. Mp 137° C.; $v_{max}$(KBr)/cm$^{-1}$ 2910 (CH), 2876 (CH), 2856 (CH), 2799 (CH), 1659 (C=O), 1596 (NO₂), 1502 (NO₂); $\delta_H$ (250 MHz; CDCl₃) 2.16 (3H, s, CH₃), 2.93 (12H, s, NCH₃), 6.59-6.62 (2H, d, J8.5, ArH), 6.69-6.71 (2H, d, J2.75, ArH), 7.08-7.47 (2H, brd s, ArH); $\delta_C$ (62.9 MHz; CDCl₃) 170.3 (C=O), 148.9 (ArC), 127.2 (ArC), 127.1 (ArC), 127.0 (ArC), 110.9 (ArC), 110.7 (ArC), 40.7 (NCH₃), 22.9 (CH₃); m/z (ES) 284.2 (100%, [M−OAc]⁺), 328.1 (15%, [M+H]⁺), 350.1 (41%, [M+Na]⁺).

Synthesis 19

3,11-Dinitro-10H-phenothiazine

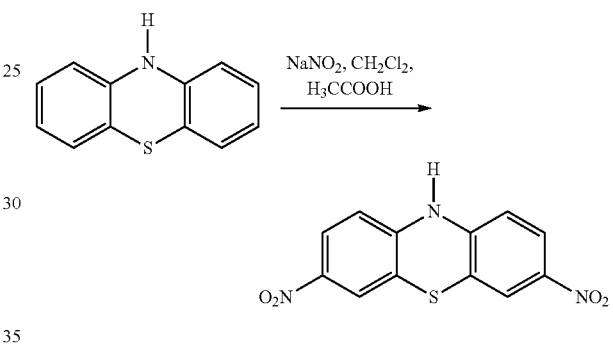

10H-Phenothiazine (20.00 g, 100 mmol), dichloromethane (100 cm³) and acetic acid (40 cm³) had sodium nitrite (20.07 g, 300 mmol) added and the mixture was stirred for 10 minutes at room temperature. Additional acetic acid (40 cm³), dichloromethane (100 cm³) and sodium nitrite (20.07 g, 300 mmol) were then added. A further 120 cm³ of acetic acid was added to try and break up the thick reaction mixture. The mixture was stirred for 3 hours. The suspension was filtered and washed with 100 cm³ each of ethanol, water, and finally ethanol to give a purple/brown solid. The residue was stirred in hot DMF and allowed to cool before filtering the dinitro product, which was washed with ethanol (150 cm³) and dried to give the title compound (24.88 g, 86%) as a brown solid; $v_{max}$(KBr)/cm$^{-1}$ 3331 (NH), 3294 (NH), 3229 (NH), 3101 (CH), 3067 (CH), 1602 (NO₂), 1558 (NO₂); $\delta_H$ (250 MHz; DMSO) 6.73-6.76 (2H, d, J9, ArH), 7.78 (2H, s, ArH), 7.89-7.85 (2H, d, J9, ArH).

Synthesis 20

1-(3,7-Bis-diethylamino-phenothiazin-10-yl)-ethanone

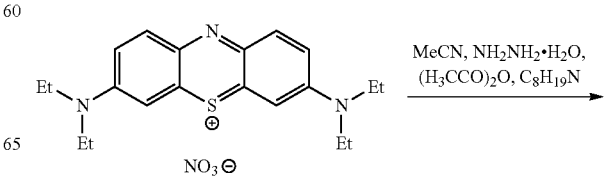

-continued

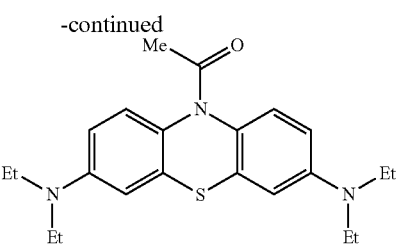

To a 250 cm³ round bottom flask under an atmosphere of nitrogen was added ethylthioninium nitrate monohydrate (7.13 mmol, 3 g) and acetonitrile (20 cm³). Hydrazine monohydrate (16.4 mmol, 0.82 g) was added and the mixture was heated to reflux and stirred for 10 minutes before cooling to 25° C. The brown solution had acetic anhydride (114 mmol, 11.65 g) and Hunig's base (diisopropylethylamine) (21.4 mmol, 2.77 g) was added. The mixture was heated at 90° C. for 2 hours. The cooled mixture was then poured carefully into ice water (40 cm³) in ten equal portions while stirring to give a precipitate. The precipitate was stirred for 30 minutes before it was filtered, washed with water (3×25 cm³) and air dried for 30 minutes. The crude material was crystallised from hot ethanol (50 cm³) to yield the title compound (1.73 g, 63%) as a light grey solid. $\delta_H$ (250 MHz; CDCl₃) 7.0-7.5 (2H, brds, ArH), 6.64 (2H, s, ArH), 6.52 (2H, d, ArH), 3.35 (8H, q, 7, NCH₂), 2.18 (3H, s, CH₃), 1.16 (12H, t, 7, CH₃); $\delta_C$ (62.9 MHz; CDCl₃) 12.5 (CH₃), 22.9 (CH₃), 44.6 (NCH₂), 110.1 (ArC), 127.4 (ArC), 146.5 (ArC), 170.2 (C=O).

Synthesis 21

N,N,N',N'-Tetraethyl-10H-phenothiazine-3,7-diamine bis(hydrogen chloride)

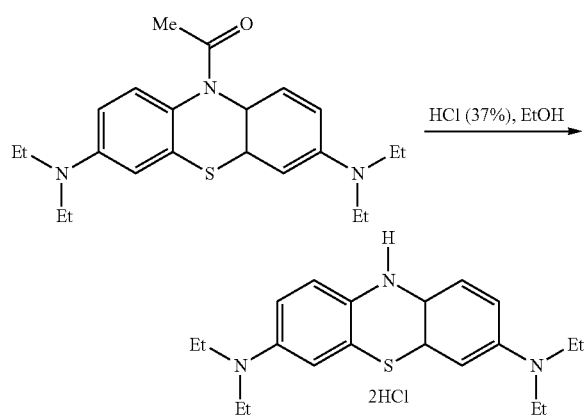

To a round bottom flask was added 1-(3,7-bis-diethylamino-phenothiazin-10-yl)-ethanone (0.5 g, 1.30 mmol), ethanol (5 cm³), and hydrochloric acid (37%, 1.3 cm³) and the solution was heated at 80° C. for 1 hour. Once cooled to room temperature, the mixture was concentrated giving the title compound (0.54 g, 100%) as a light green glass. $\delta_H$ (250 MHz; CD₃OD) 7.07 (4H, brd, ArH), 6.65 (2H, brd, ArH), 3.35 (8H, brd, NCH₂), 0.97 (12H, brd, CH₃); $\delta_C$ (62.9 MHz; CD₃OD) 10.8 (CH₃), 55.1 (NCH₂), 116.6 (ArC), 120.4 (ArC), 121.5 (ArC), 123.6 (ArC), 132.6 (ArC), 144.5 (ArC).

Synthesis 22

N,N,N',N'-Tetraethyl-10H-phenothiazine-3,7-diamine bis(hydrogen bromide)

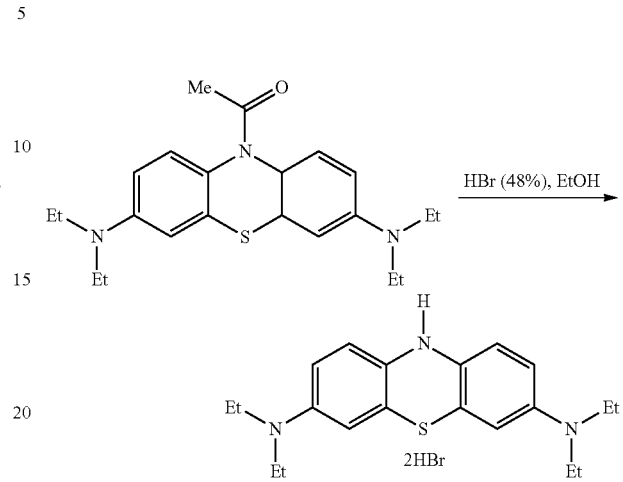

To a round bottom flask was added 1-(3,7-bis-diethylamino-phenothiazin-10-yl)-ethanone (0.5 g, 1.30 mmol), ethanol (5 cm³), and hydrobromic acid (48%, 0.75 cm³) and the solution was heated at 80° C. for 1 hour. Once cooled to room temperature, the mixture was concentrated giving the title compound (0.65 g, 100%) as a light yellow glass. $\delta_H$ (250 MHz; D₂O) 7.05 (4H, brd, ArH), 6.79 (2H, brd d, ArH), 3.43 (8H, brd, NCH₂), 1.05 (12H, brd t, CH₃); $\delta_C$ (62.9 MHz; D₂O) 12.3 (CH₃), 56.2 (NCH₂), 117.9 (ArC), 121.4 (ArC), 122.4 (ArC), 124.5 (ArC), 133.5 (ArC), 145.1 (ArC).

Synthesis 23

N,N,N',N'-Tetramethyl-10H-phenothiazine-3,7-diamine bis(hydrogen chloride)

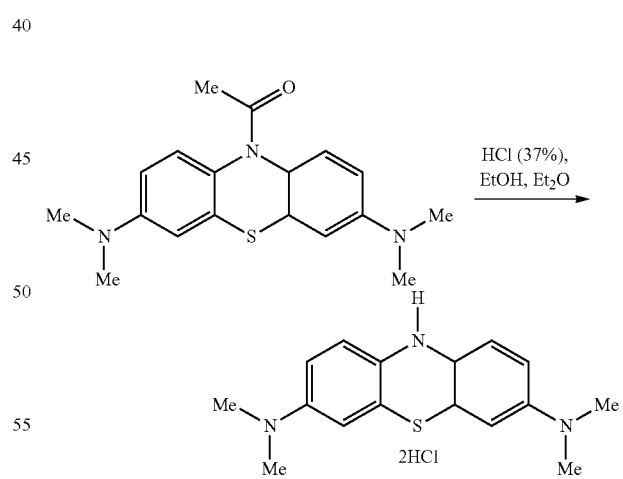

To a round bottom flask was added 1-(3,7-bis-dimethylamino-phenothiazin-10-yl)-ethanone (1 g, 3.05 mmol), ethanol (10 cm³), and hydrochloric acid (37%, 3 cm³) and the solution was heated at 80° C. for 1 hour. Once cooled to room temperature, diethyl ether was added while stirring until a constant turbid solution was obtained. After some time, a precipitate formed, which was filtered and washed with diethyl ether (10 cm³) giving the title compound (0.98 g, 90%) as a light green solid. Mp (dec) 230° C.; $\nu_{max}$(KBr)/ cm$^{-1}$ 3500-3229 (NH), 3061 (CH), 3021 (CH), 2948 (CH), 2879 (CH), 2679 (CH), 2601 (CH), 1604 (CH), 1483 (CH), 1318 (CH); δ$_H$ (250 MHz; D$_2$O) 3.18 (12H, s, NCH$_3$), 6.67 (2H, d, J8.5, ArH), 7.16 (4H, brd s, ArH); δ$_C$ (62.9 MHz; D$_2$O) 144.3 (ArC), 138.9 (ArC), 122.4 (ArC), 120.8 (ArC), 120.7 (ArC), 117.6 (ArC), 48.9 (NCH$_3$); m/z (ES) 286.1 (100%, [M−H, 2Cl]$^+$), 285.1 (40%), 284.1 (41%, [M−3H, 2Cl]$^+$).

Synthesis 24

N,N,N',N'-Tetramethyl-10H-phenothiazine-3,7-diamine bis(hydrogen bromide)

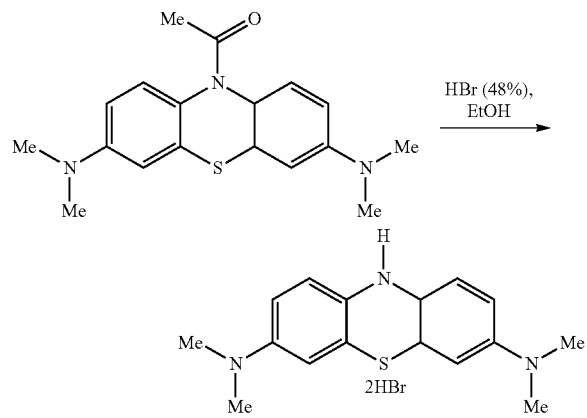

To a round bottom flask was added 1-(3,7-bis-dimethyl-amino-phenothiazin-10-yl)-ethanone (1 g, 3.05 mmol), ethanol (10 cm$^3$), and hydrobromic acid (48%, 4 cm$^3$) and the solution was heated at 80° C. for 1 hour. Once cooled to room temperature, a precipitate formed, which was filtered and washed with diethyl ether (10 cm$^3$) giving the product (1.22 g, 89%) as a light mustard solid. Mp (dec) 230° C.; ν$_{max}$(KBr)/cm$^{-1}$ 3500-3229 (NH), 3061 (CH), 3021 (CH), 2948 (CH), 2879 (CH), 2679 (CH), 2601 (CH), 1604 (CH), 1483 (CH), 1318 (CH); δ$_H$ (250 MHz; D$_2$O) 3.18 (12H, s, NCH$_3$), 6.66 (2H, d, J8.75, ArH), 7.15 (4H, s, ArH); δ$_C$ (62.9 MHz; D$_2$O) 144.3 (ArC), 138.9 (ArC), 122.4 (ArC), 120.8 (ArC), 120.7 (ArC), 117.6 (ArC), 48.9 (NCH$_3$).

Synthesis 25

N,N,N',N'-Tetraethyl-10H-phenothiazine-3,7-diamine bis(hydrogen bromide)

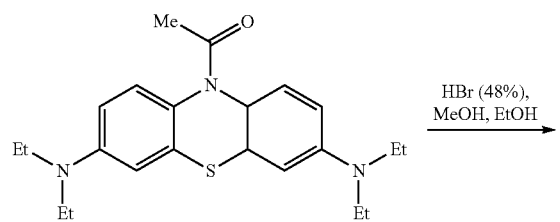

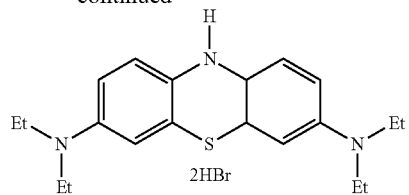

To a round bottom flask was added 1-(3,7-bis-diethyl-amino-phenothiazin-10-yl)-ethanone (1.0 g, 2.60 mmol), methanol (10 cm$^3$), and hydrobromic acid (48%, 2.94 cm$^3$) and the solution was heated at 80° C. for 1 hour. Once cooled to 5° C., the mixture had diethyl ether added, giving a cloudy solution. The solution was stirred for 30 minutes and gave the title compound (0.83 g, 63%) as a light yellow solid. δ$_H$ (250 MHz; D$_2$O) 7.05 (4H, brd, ArH), 6.79 (2H, brd d, ArH), 3.43 (8H, brd, NCH$_2$), 1.05 (12H, brd t, CH$_3$); δ$_C$ (62.9 MHz; D$_2$O) 12.3 (CH$_3$), 56.2 (NCH$_2$), 117.9 (ArC), 121.4 (ArC), 122.4 (ArC), 124.5 (ArC), 133.5 (ArC), 145.1 (ArC).

Stability Studies

The DAPTZ compounds of the present invention are stably reduced (i.e., are in a stably reduced form). For example, they are stable in the solid form, for example, for at least 1 week, e.g., at least 2 weeks, e.g., at least 1 month, e.g., at least 2 months, e.g., at least 1 year (e.g., at room temperature, e.g., 18-25° C., e.g., in a sealed container).

One sample of compound B3 (N,N,N',N'-Tetramethyl-10H-phenothiazine-3,7-diamine bis(hydrogen chloride)), in solid form, was found to be substantially reduced even after 2 years in storage.

Once the DAPTZ compounds are dissolved in water (i.e., in the form of an aqueous solution), they slowly oxidize (giving the solution a blue colour), typically over a period of 1 to 3 hours.

The stability of two DAPTZ compounds of the present invention was studied, specifically, B3 (N,N,N',N'-Tetramethyl-10H-phenothiazine-3,7-diamine bis(hydrogen chloride)), and B6 (N,N,N',N'-Tetramethyl-10H-phenothiazine-3,7-diamine bis(hydrogen iodide)). MTC was used as a standard.

The compounds were weighed into universal containers. Enough water was added to yield a 1 mM solution, and the mixture stirred to dissolve the solid. The absorbance was determined at 610 nm and 665 nm for 50 μL samples (in triplicate) of each of the solutions at various time points. The initial time point taken was at 10 minutes as the compounds took time to dissolve completely. A UV/visible spectrum was also recorded at time points 20 minutes, 3 hours, and 18 hours.

The percent reduced form (%) was calculated assuming that the 10 minute reading for MTC represented 0% reduced, and that a blank represented 100% reduced (colourless).

FIG. 1 is a graph of the percent reduced form (%) versus time (minutes) for each of three compounds, B1, B3, and B6, as determined using absorbance at 665 nm.

Figure 2:
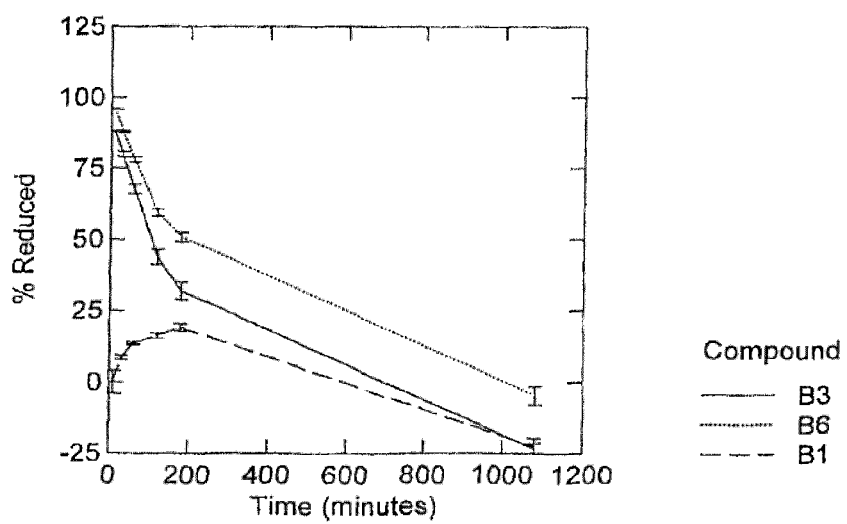
FIG. 2 is a graph of the percent reduced form (%) versus time (minutes) for each of three compounds, B1, B3, and B6, as determined using absorbance at 610 nm.

FIG. 2 is a graph of the percent reduced form (%) versus time (minutes) for each of three compounds, B1, B3, and B6, as determined using absorbance at 610 nm.

Figure 3A:
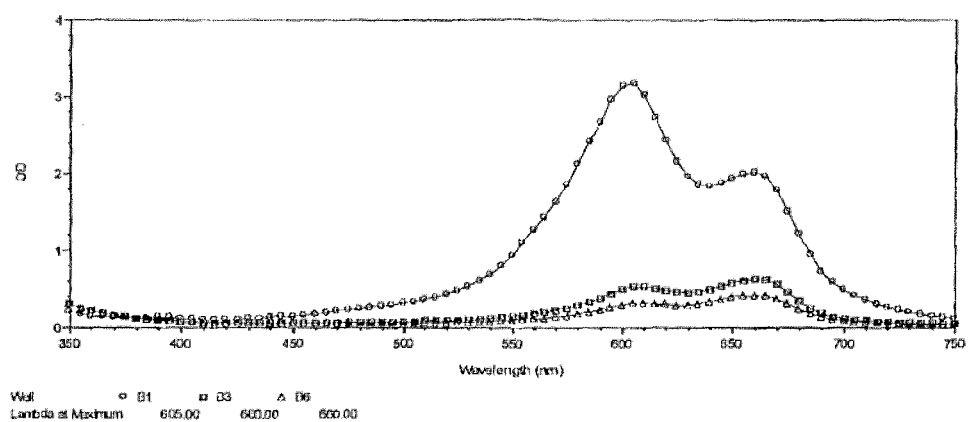
FIG. 3A shows the UV/visible absorption spectra for aqueous samples of each of three compounds, B1 (open circles, maximum at 605 nm), B3 (open squares, maximum at 660 nm), and B6 (open triangles, maximum at 660 nm), after 20 minutes.
Figure 3B:
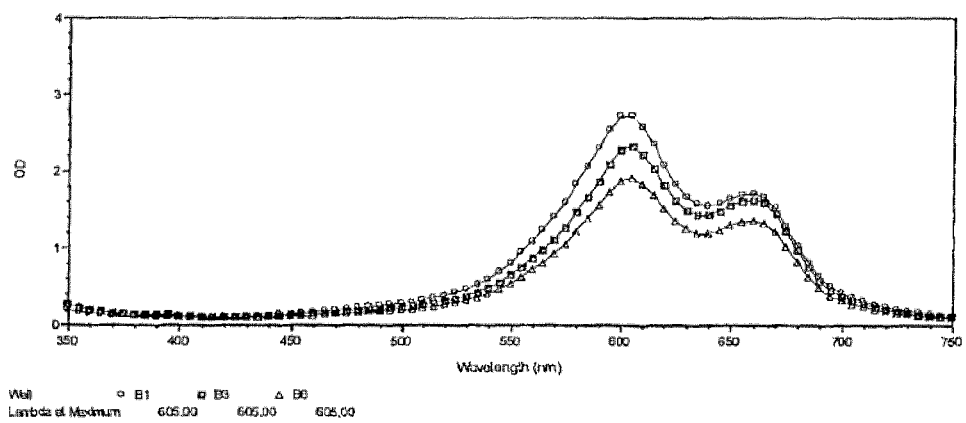
FIG. 3B shows the UV/visible absorption spectra for aqueous samples of each of three compounds, B1 (open circles, maximum at 605 nm), B3 (open squares, maximum at 605 nm), and B6 (open triangles, maximum at 605 nm), after 3 hours.
Figure 3C:
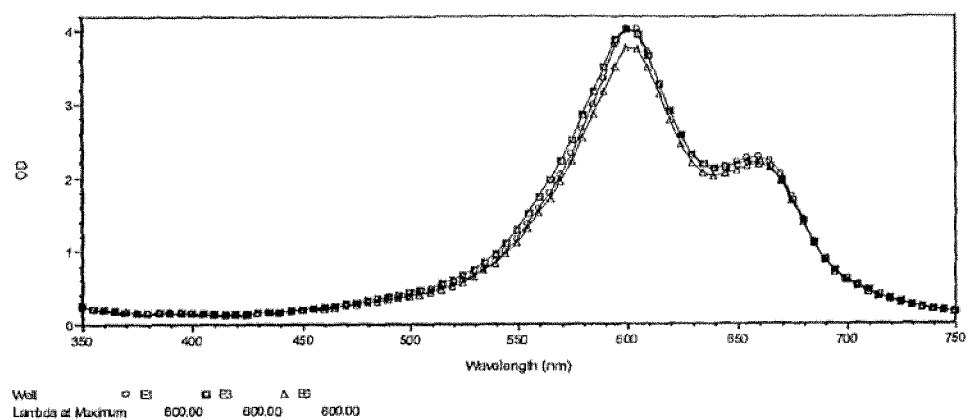
FIG. 3C shows the UV/visible absorption spectra for aqueous samples of each of three compounds, B1 (open circles, maximum at 605 nm), B3 (open squares, maximum at 605 nm), and B6 (open triangles, maximum at 605 nm), after 28 hours.

FIGS. 3A, 3B, and 3C show the UV/visible absorption spectra for aqueous samples of each of three compounds, B1 (open circles), B3 (open squares), and B6 (open triangles), after 20 minutes (FIG. 3A), 3 hours (FIG. 3B), and 18 hours (FIG. 3C).

These data demonstrate that the DAPTZ compounds (stabilized reduced forms) remain substantially stable (>50%) for at least 1 hour, and that compound B6 remains substantially stable (>50%) for almost 3 hours. However, after about 18 hours, the compounds are not significantly different from MTC. See, for example, FIG. 3C, where the spectra are almost indistinguishable.

Additionally, the rate of autoxidation was found to be slower for the "iodide" compound (Compound B6) as compared to the "chloride" compound (Compound B3), suggesting that the rate of autoxidation depends upon the counterion. Although the difference in rate was small, it may be significant in drug formulation. Other salts may be more stable against oxidation.

A batch of N,N,N',N'-tetramethyl-10H-phenothiazine-3,7-diamine bis(hydrogen bromide) was prepared in April 2006 and analysed by NMR. After 10 months of storage in the dark at room temperature, the solid material was analysed once more and the NMR data was found to be identical. The colour of the solid remained consistent over time. It appears that the molecule, in this form, is stable under these conditions over this time period.

Biological Studies

Methods: In Vitro Assay for Establishing B50

These methods are described in detail in WO 96/30766. Briefly, a fragment of tau corresponding to the core repeat domain, which has been adsorbed to a solid phase substrate, is able to capture soluble full-length tau and bind tau with high affinity. This association confers stability against proteolytic digestion of the aggregated tau molecules. The process is self-propagating, and can be blocked selectively by prototype pharmaceutical agents.

More specifically, truncated tau (residues 297-390; dGA) diluted in carbonate buffer (pH 9.6) was bound to the assay plate, and full-length tau (T40) was added in the aqueous phase. The aqueous phase binding buffer contained 0.05% Tween-20 and 1% gelatine in phosphate-buffered saline (pH 7.4). Bound tau was detected using mAb 499 that recognises an N-terminal epitope within the aqueous phase full-length tau but that fails to recognise the solid phase-bound truncated tau fragment.

The concentration of compound required to inhibit the tau-tau binding by 50% is referred to as the B50 value.

Methods: Cell-Based Assay for Establishing EC50

These methods are described in more detail in WO 02/055720. Briefly, fibroblast cells (3T6) express full-length tau ("T40") under control of an inducible promoter, and low constitutive levels of the PHF-core tau fragment (12 kD fragment). When T40 expression is induced, it undergoes aggregation-dependent truncation within the cell, N-terminally at ~αα 295 and C-terminally at ~αα390, thereby producing higher levels of the 12 kD PHF-core domain fragment. Production of the 12 kD fragment can be blocked in a dose-dependent manner by tau-aggregation inhibitors. Indeed, the quantitation of inhibitory activity of compounds with respect to proteolytic generation of the 12 kD fragment within cells can be described entirely in terms of the same parameters that describe inhibition of tau-tau binding in vitro. That is, the extent of proteolytic generation of the 12 kD fragment within cells is determined entirely by the extent of tau-tau binding through the repeat domain. The availability of the relevant proteases within the cell is non-limiting.

Results are expressed as the concentration at which there is a 50% inhibition of generation of the 12 kD fragment. This is referred to as the EC50 value.

Methods: Toxicity in Cells (LD50) and Therapeutic Index (RxI)

Toxicity of the compounds described herein was assessed in the cell based assay used to assess EC50. Toxicity was measured by cell numbers determined after 24 hours exposure to the compound using a lactate dehydrogenase assay kit TOX-7 (Sigma Biosciences) according to the manufacturer's instructions after lysis of remaining cells. Alternatively, a kit from Promega UK (CytoTox 96) was used, again according to the manufacturer's instructions.

The therapeutic index (RxI) was calculated as: RxI=LD50/EC50.

The data are summarised in the following Table.

| Biological Data | | | | |
|---|---|---|---|---|
| Compound | B50 | EC50 | LD50 | RxI |
| B3 | 57.3 | 0.50 | 44.0 | 88 |
| B4 | 23.5 | 2.23 | — | — |
| B6 | 494 | 0.38 | 115 | 303 |
| MTC | 218 | 0.59 | 65.0 | 110 |

B3: N,N,N',N'-Tetramethyl-10H-phenothiazine-3,7-diamine bis(hydrogen chloride).
B4: 10H-phenothiazine-3,7-diamine bis(hydrogen chloride).
B6: N,N,N',N'-Tetramethyl-10H-phenothiazine-3,7-diamine bis(hydrogen iodide).
MTC: Methylthioninium chloride.

Partition Coefficient Studies

It is well known that the partition coefficient for a drug in an organic phase/water system (typically an n-octanol/water system), usually reported as the logarithm (i.e., $\log_{10}P$), is a good indicator for the biological activity of that drug. See, e.g., Hansch, C., et al., 1964, J. Am. Chem. Soc., Vol. 86, pp. 1616-1626; Kubinyi, H., 1977, J. Med. Chem., Vol. 20, pp. 625-629. It is believed that this is because the absorption of a compound depends on its partition between the biological membrane and the aqueous phase. Partition coefficients are also useful in separation techniques and in the prediction of the solubility of drugs.

In the context of drug-like substances, hydrophobicity is related to absorption, bioavailability, hydrophobic drug-receptor interactions, metabolism, and toxicity. Low hydrophilicities, and therefore high $\log_{10}P$ values, may cause poor absorption or permeation. It has been shown for compounds to have a reasonable probability of being well absorbed, their $\log_{10}P$ value must not be greater than 5.0. The distribution of calculated $\log_{10}P$ values of more than 3000 drugs on the market underlines this fact.

Many methods for determining partition coefficients are known. In this study, aqueous solutions of selected compounds were shaken with n-octanol and aliquots concentrations in each phase determined by visible spectrophotometry. The $\log_{10}P$ was then calculated for each compound, using the following formula:

$$\log_{10}P = \log_{10}[\text{Drug}]_{octanol} - \log_{10}[\text{Drug}]_{water} = \log_{10}([\text{Drug}]_{octanol}/[\text{Drug}]_{water})$$

The data are summarised in the following table. The DAPTZ compounds of the present invention were found to have $\log_{10}P$ values expected for drug-like molecules.

| Partition Coefficient Data | | | | |
|---|---|---|---|---|
| Compound | $\lambda_{max}$ (octanol/water) | Absorbance for n-octanol phase | Absorbance for water phase | $\log_{10}P$ |
| MTC | 665/660 | 0.217 | 4.83 | −1.35 |
| B3 | 664/660 | 0.083 | 0.111 | −0.13 |
| B6 | 658.4/662.4 | 0.179 | 0.563 | −0.498 |

B3: N,N,N',N'-Tetramethyl-10H-phenothiazine-3,7-diamine bis(hydrogen chloride).
B6: N,N,N',N'-Tetramethyl-10H-phenothiazine-3,7-diamine bis(hydrogen iodide).
MTC: Methylthioninium chloride.

Crystal Structure

Figure 4:
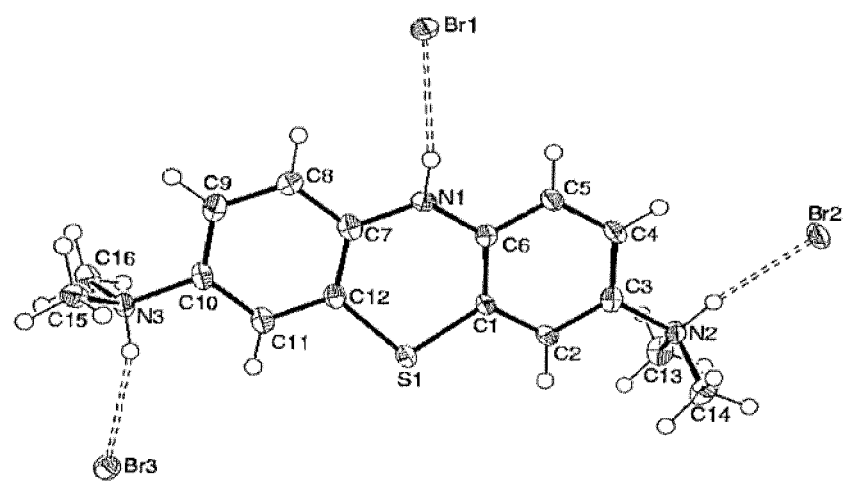
FIG. 4 shows the crystal structure of N,N,N',N'-tetramethyl-10H-phenothiazine-3,7-diamine bis(hydrogen bromide).

FIG. 4 shows the crystal structure of N,N,N',N'-tetramethyl-10H-phenothiazine-3,7-diamine bis(hydrogen bromide). The crystal structure shows three crystallographically distinct bromide ions. Br1 and Br2 occupy special positions with 2-fold symmetry, whereas the organic main molecule and Br3 occupy general positions. Hence, the overall stoichiometry is $C_{16}H_{21}N_3SBr_2$.

Figure 5:
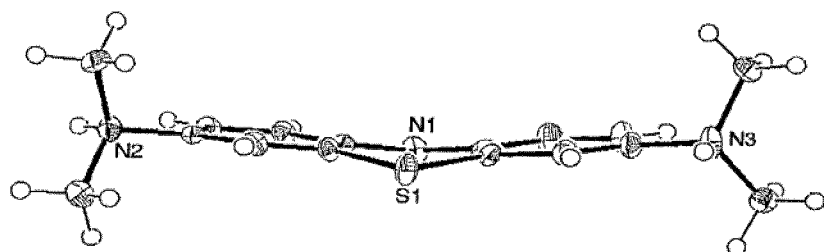
FIG. 5 shows the side-on view of N,N,N',N'-tetramethyl-10H-phenothiazine-3,7-diamine bis(hydrogen bromide).

FIG. 5 shows the side-on view of N,N,N',N'-tetramethyl-10H-phenothiazine-3,7-diamine bis(hydrogen bromide) and reveals the non-planarity; the dihedral angle between the outer benzene rings is 11.0 (3) degrees.

Figure 6:
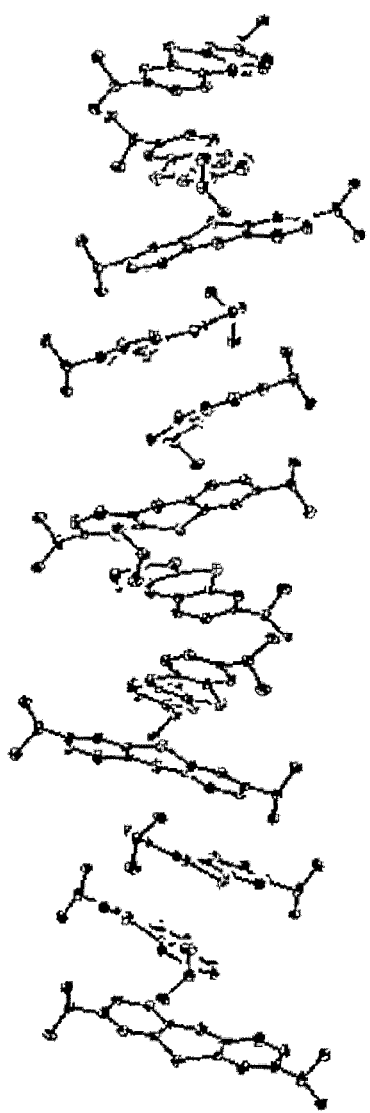
FIG. 6 shows part of one helical column of N,N,N',N'-tetramethyl-10H-phenothiazine-3,7-diamine bis(hydrogen bromide) molecules in the crystal.

FIG. 6 shows part of one helical column of N,N,N',N'-tetramethyl-10H-phenothiazine-3,7-diamine bis(hydrogen bromide) molecules in the crystal.

What is claimed is:

1. A method of treating a disease of protein aggregation in a subject in need thereof, wherein the protein is selected from huntingtin, α-synuclein, and superoxide dismutase, the method comprising administering to a subject with a disease of protein aggregation, wherein the protein is selected from huntingtin, α-synuclein, and superoxide dismutase, a therapeutically effective amount of a bis protic acid salt compound of the following formula:

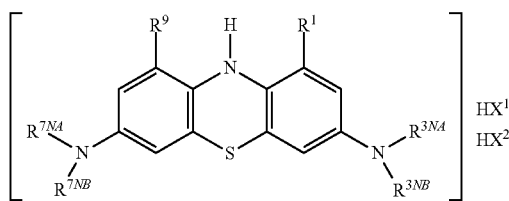

wherein:
each of $R^1$ and $R^9$ is independently selected from: —H, $C_{1-4}$alkyl, $C_{2-4}$alkenyl, and halogenated $C_{1-4}$alkyl;
each of $R^{3NA}$ and $R^{3NB}$ is independently selected from: —H, $C_{1-4}$alkyl, $C_{2-4}$alkenyl, and halogenated $C_{1-4}$alkyl;
each of $R^{7NA}$ and $R^{7NB}$ is independently selected from: —H, $C_{1-4}$alkyl, $C_{2-4}$alkenyl, and halogenated $C_{1-4}$alkyl; and
each of $HX^1$ and $HX^2$ is independently a protic acid, wherein if any of $HX^1$ or $HX^2$ is a hydrohalic acid, then each is independently selected from HCl and HBr; thereby inhibiting aggregation of huntingtin, α-synuclein, or superoxide dismutase.

2. The method of claim 1, wherein the administering is oral.

3. The method of claim 1, wherein the protein is huntingtin.

4. The method of claim 1, wherein the protein is α-synuclein.

5. The method of claim 1, wherein the protein is superoxide dismutase.

6. A method of treating Huntington's disease, Parkinson's disease, amyotrophic lateral sclerosis, or multiple system atrophy in a subject in need thereof, the method comprising administering to a subject with Huntington's disease, Parkinson's disease, amyotrophic lateral sclerosis, or multiple system atrophy a therapeutically effective amount of a bis acid protic salt compound of the following formula:

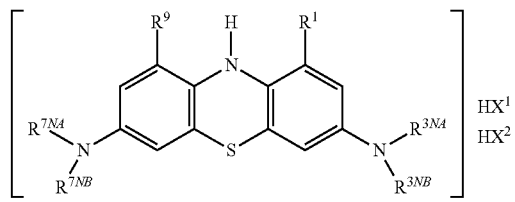

wherein:
each of $R^1$ and $R^9$ is independently selected from: —H, $C_{1-4}$alkyl, $C_{2-4}$alkenyl, and halogenated $C_{1-4}$alkyl;
each of $R^{3NA}$ and $R^{3NB}$ is independently selected from: —H, $C_{1-4}$alkyl, $C_{2-4}$alkenyl, and halogenated $C_{1-4}$alkyl;
each of $R^{7NA}$ and $R^{7NB}$ is independently selected from: —H, $C_{1-4}$alkyl, $C_{2-4}$alkenyl, and halogenated $C_{1-4}$alkyl; and
each of $HX^1$ and $HX^2$ is independently a protic acid, wherein if any of $HX^1$ or $HX^2$ is a hydrohalic acid, then each is independently selected from HCl and HBr; thereby treating the subject's Huntington's disease, Parkinson's disease, amyotrophic lateral sclerosis, or multiple system atrophy.

7. The method of claim 6, wherein the administering is oral.

8. The method of claim 6, wherein the disease is Huntington's disease.

9. The method of claim 6, wherein the disease is Parkinson's disease.

10. The method of claim 6, wherein the disease is amyotrophic lateral sclerosis.

11. The method of claim 6, wherein the disease is multiple system atrophy.

* * * * *